(12) United States Patent
Yoon et al.

(10) Patent No.: US 11,280,034 B2
(45) Date of Patent: Mar. 22, 2022

(54) NANOFIBROUS CARBON MICROSTRUCTURES

(71) Applicant: University of Florida Research Foundation, Inc., Gainesville, FL (US)

(72) Inventors: Yong-Kyu Yoon, Gainesville, FL (US); Pit Fee Jao, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 103 days.

(21) Appl. No.: 15/301,620

(22) PCT Filed: Apr. 2, 2015

(86) PCT No.: PCT/US2015/024141
§ 371 (c)(1),
(2) Date: Oct. 3, 2016

(87) PCT Pub. No.: WO2015/153907
PCT Pub. Date: Oct. 8, 2015

(65) Prior Publication Data
US 2017/0183798 A1 Jun. 29, 2017

Related U.S. Application Data

(60) Provisional application No. 61/975,451, filed on Apr. 4, 2014.

(51) Int. Cl.
*D04H 1/728* (2012.01)
*A61N 1/05* (2006.01)
(Continued)

(52) U.S. Cl.
CPC .............. *D04H 1/728* (2013.01); *A61N 1/04* (2013.01); *A61N 1/05* (2013.01); *B06B 1/02* (2013.01);
(Continued)

(58) Field of Classification Search
None
See application file for complete search history.

(56) References Cited

U.S. PATENT DOCUMENTS 7,351,052 B2 4/2008 Chun et al.
8,066,932 B2 11/2011 Xu
(Continued)

FOREIGN PATENT DOCUMENTS

WO 2010002045 A1 1/2010

OTHER PUBLICATIONS

A. D. Campo, C. Greiner, "SU-8: A photoresist for high-aspect-ratio and 3D submicron lithography", J. Micromech. Microeng., vol. 17, No. 6, pp. 81-95, 2007.*
(Continued)

*Primary Examiner* — Erica S Lee
(74) *Attorney, Agent, or Firm* — Thomas | Horstemeyer, LLP

(57) ABSTRACT

Various examples of methods and systems related to nanofibrous microstructures including carbon nanofibrous microelectrode arrays are provided. In one example, a method includes electrospinning photosensitive nanofibers on a patterned substrate; immersing the photosensitive nanofibers in a refractive index matching medium; and exposing the immersed photosensitive nanofibers to ultraviolet (UV) light through the patterned substrate or through a front side photomask. In another example, a microelectrode array includes a carbon thin film (CTF) trace pattern including a plurality of CTF electrode pads; and a plurality of carbon nanofiber (CNF) pillars disposed on the plurality of CTF electrode pads.

20 Claims, 16 Drawing Sheets

(51) Int. Cl.
  *G03F 7/20* (2006.01)
  *G03F 7/00* (2006.01)
  *G03F 7/038* (2006.01)
  *C01B 32/16* (2017.01)
  *A61N 1/04* (2006.01)
  *B06B 1/02* (2006.01)
  *B82Y 40/00* (2011.01)
  *D01D 5/38* (2006.01)
  *B82Y 20/00* (2011.01)
  *A61B 5/24* (2021.01)

(52) U.S. Cl.
  CPC .............. *B82Y 40/00* (2013.01); *C01B 32/16* (2017.08); *D01D 5/38* (2013.01); *G03F 7/0035* (2013.01); *G03F 7/0037* (2013.01); *G03F 7/038* (2013.01); *G03F 7/2014* (2013.01); *G03F 7/2022* (2013.01); *A61B 5/24* (2021.01); *A61B 2562/125* (2013.01); *B82Y 20/00* (2013.01)

(56) References Cited

U.S. PATENT DOCUMENTS

| | | | | |
|---|---|---|---|---|
| 2004/0176828 | A1* | 9/2004 | O'Brien | A61N 1/05 607/119 |
| 2004/0185349 | A1* | 9/2004 | Yang | G03F 1/50 430/5 |
| 2008/0131817 | A1* | 6/2008 | Yoon | G03F 7/70341 430/319 |
| 2011/0177332 | A1 | 7/2011 | Park et al. | |
| 2011/0195361 | A1* | 8/2011 | Rock | G03F 1/50 430/322 |
| 2011/0214487 | A1 | 9/2011 | Olesik et al. | |
| 2012/0125213 | A1* | 5/2012 | Koo | B41N 1/06 101/395 |
| 2012/0274004 | A1 | 11/2012 | Kobrin | |
| 2012/0319329 | A1* | 12/2012 | Chen | B81C 1/00031 264/320 |
| 2014/0152143 | A1* | 6/2014 | Rogers | B81C 1/00095 310/309 |
| 2015/0221689 | A1* | 8/2015 | Lee | H01L 27/14643 257/292 |
| 2015/0257283 | A1* | 9/2015 | Ellinger | H01L 29/42384 427/97.5 |
| 2016/0195488 | A1* | 7/2016 | Ensor | G01N 33/0047 422/69 |

OTHER PUBLICATIONS

C. S. Sharma, A. Sharma, M. Madou, "Multiscale carbon structures fabricated by direct micropatterning of electrospun mats of SU-8 photoresist nanofibers", Langmuir, vol. 26, No. 4, pp. 2218-2222, 2010.*

International Search Report for PCT/US2015/024141 dated Jun. 24, 2015.

Jao, et al., "Fabrication of Carbon Nanofibrous Microelectrode Array (CNF-MEA) Using Nanofiber Immersion Photolithography", MEMS 2014, San Francisco, CA, USA Jan. 26-30, 2014, pp. 498-501.

Sundararaghavan, et al., "Electrospun Fibrous Scaffolds with Multiscale and Photopatterned Porosity", Macromolecular Bioscience, 2010, 10, 265-270.

Lee, et al., "Fabrication of Nanofiber Microarchitectures Localized within Hydrogel Microparticles and Their Application to Protein Delivery and Cell Encapsulation", Advanced Functional Materials, 2012, DOI: 10.1002/adfm.201201501, pp. 1-7.

Shi, et al., "Microcontact Printing and Lithographic Patterning of Electrospun Nanofibers", Langmuir Letter, American Chemical Society, 2009, 25(11), 6015-6018.

Sharma, et al., "Multiscale Carbon Structures Fabricated by Direct Micropatterning of Electrospun Mates of SU-8 Photoresist Nanofibers", Langmuir Letter, American Chemical Society, 2010, 26(4), 2218-2222.

Lim, et al., "Micropatterning and characterization of electrospun poly(ϵ-caprolactone)/gelatin nanofiber tissue scaffolds by femtosecond laser ablation for tissue engineering applications", Biotechnology and Bioengineering, vol. 108, No. 1, Jan. 1, 2011, pp. 116-126.

H. J. Lee, H.-S. Kim, H. O. Kim, and W.-G. Koh, "Micropatterns of double-layered nanofiber scaffolds with dual functions of cell patterning and metabolite detection.," Lab on a Chip, vol. 11, No. 17, pp. 2849-2857, 2011.

Del Campo, et al., "SU-8: a photoresist for high-aspect-ratio and 3D submicron lithography", Journal of Micromechanics and Microengineering, Published May 15, 2007, 81-95, 16 pages.

Chuang, et al., "Reduction of diffraction effect of UV exposure on SU-8 negative thick photoresist by air gap elimination", Microsystem Technologies 8, 2002, 308-313, 6 pages.

\* cited by examiner

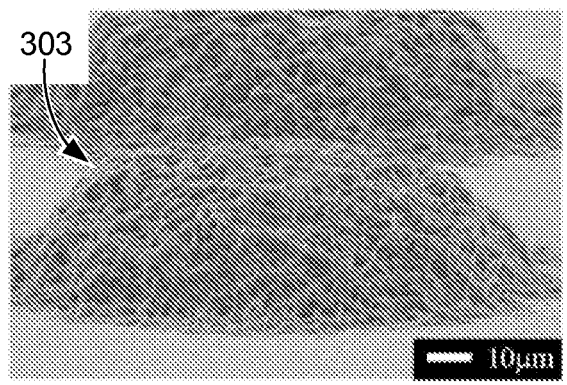 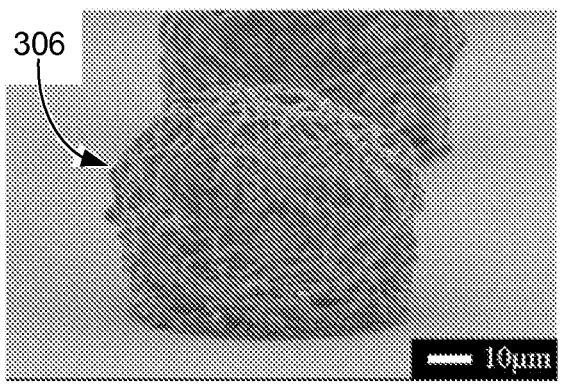
FIG. 3A  FIG. 3B
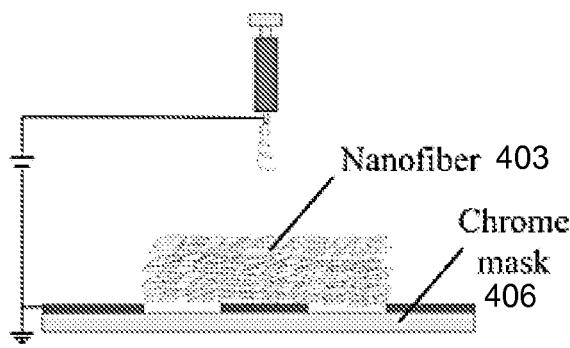
FIG. 4A
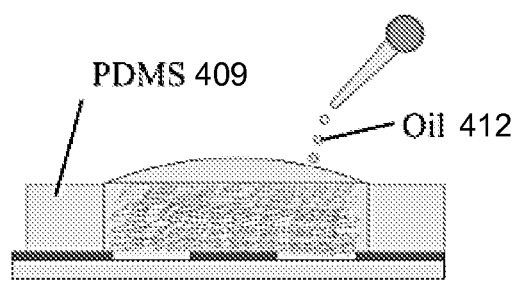
FIG. 4B
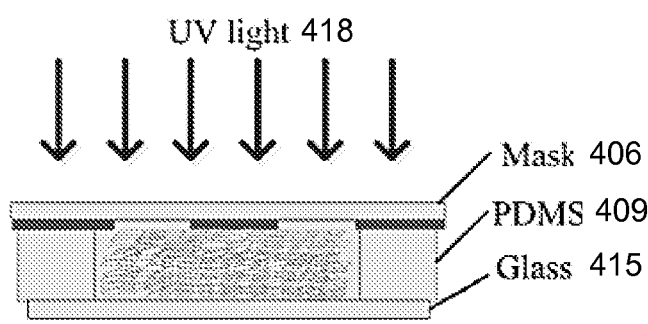
FIG. 4C

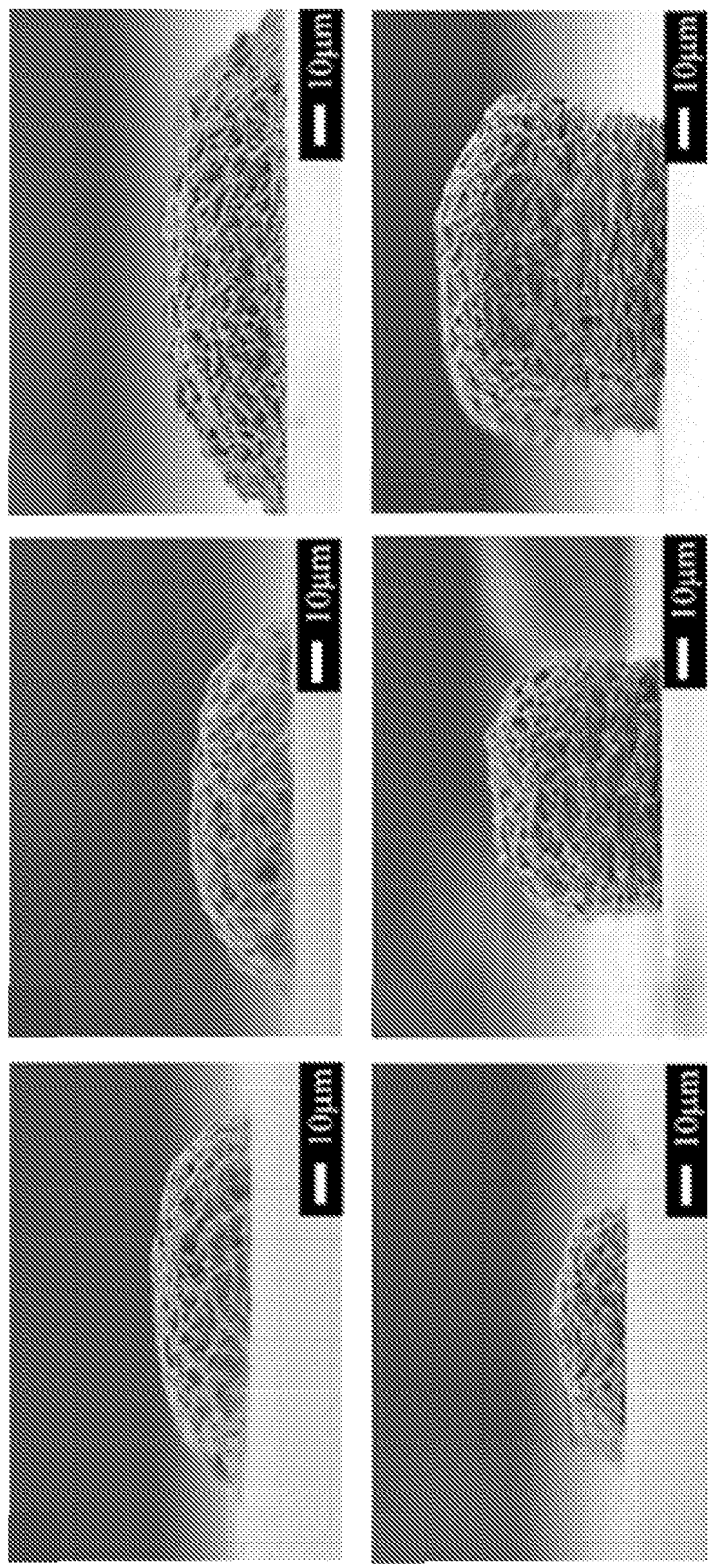

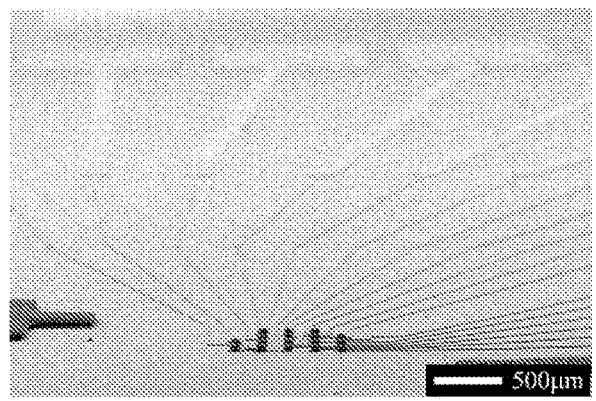 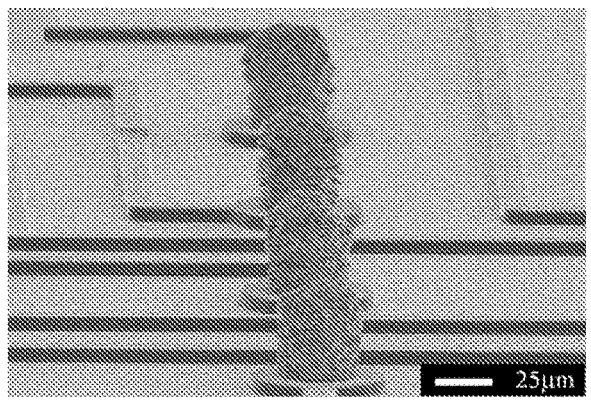
FIG. 12A  FIG. 12B
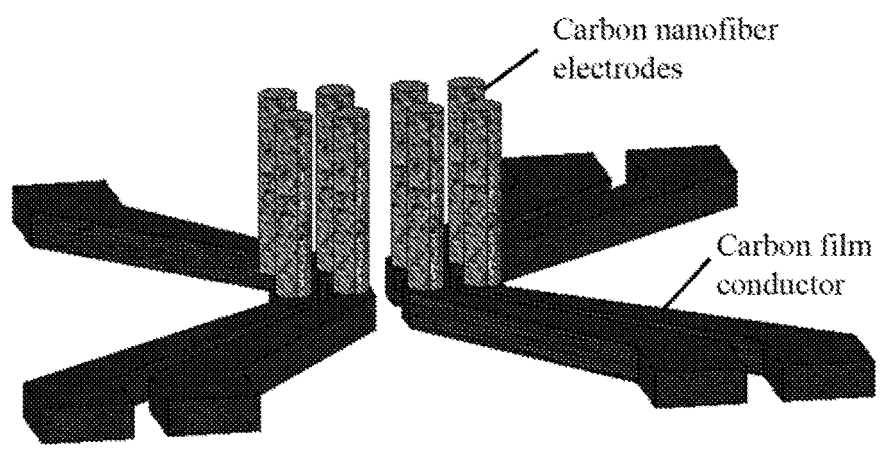
FIG. 13

FIG. 15A
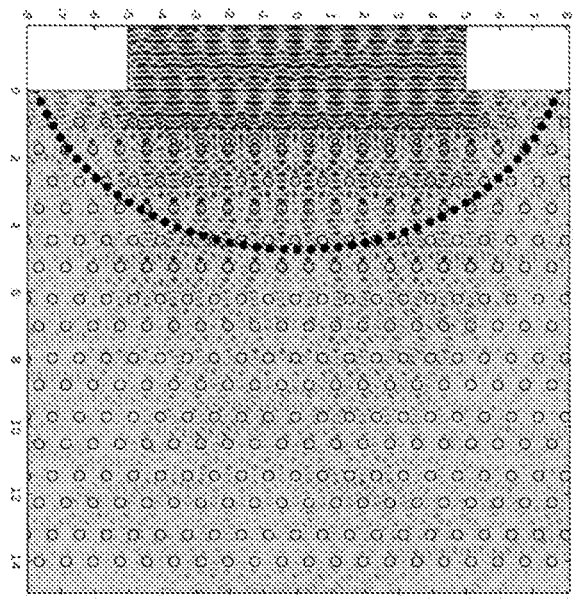
FIG. 15B
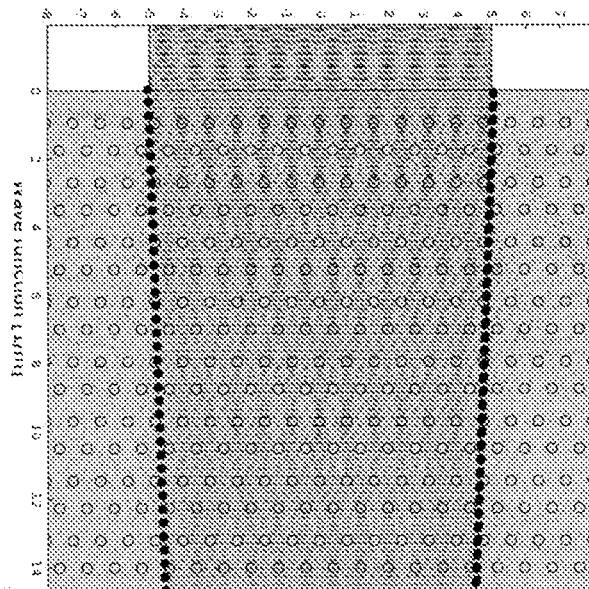
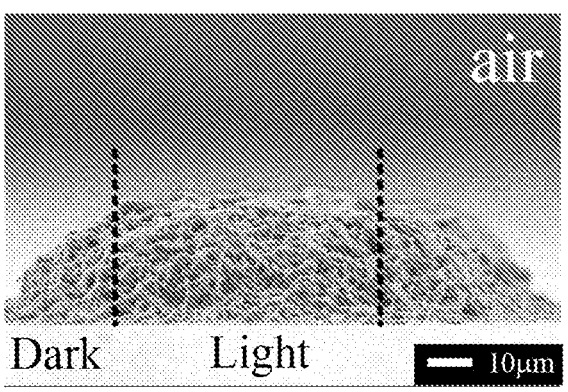
FIG. 15C
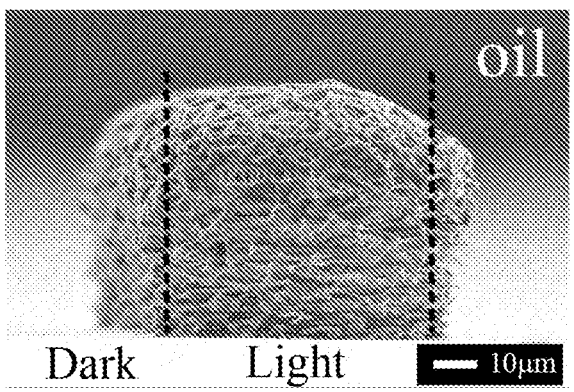
FIG. 15D

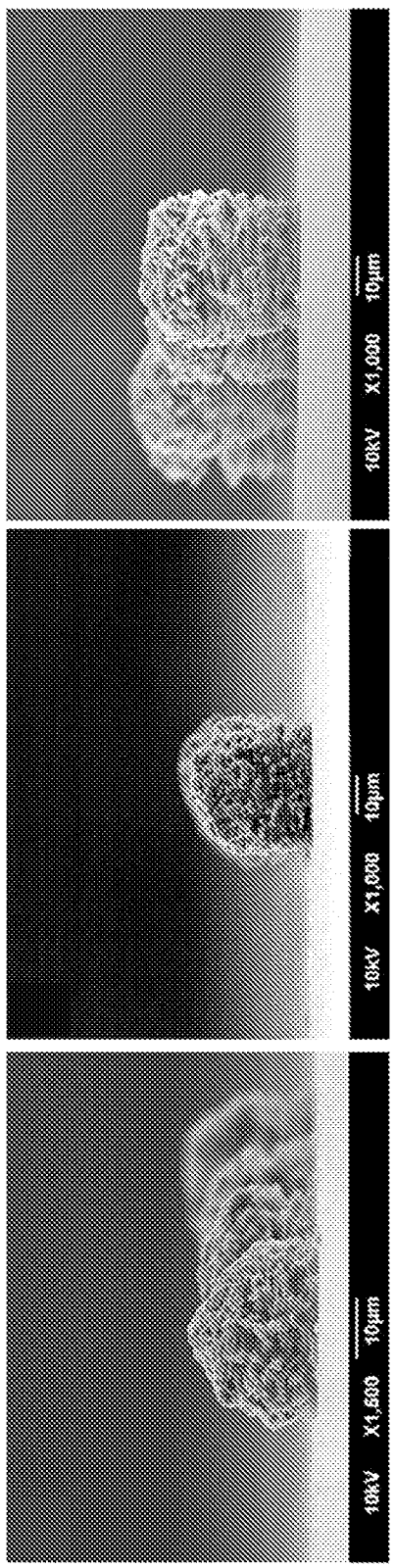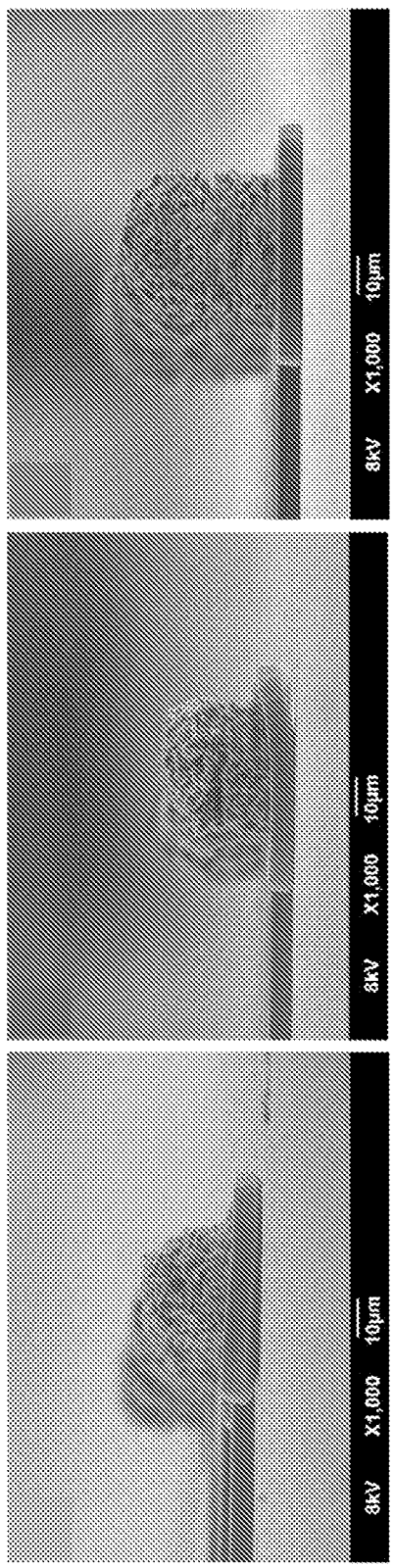
FIG. 17A　FIG. 17B　FIG. 17C　FIG. 17D　FIG. 17E　FIG. 17F

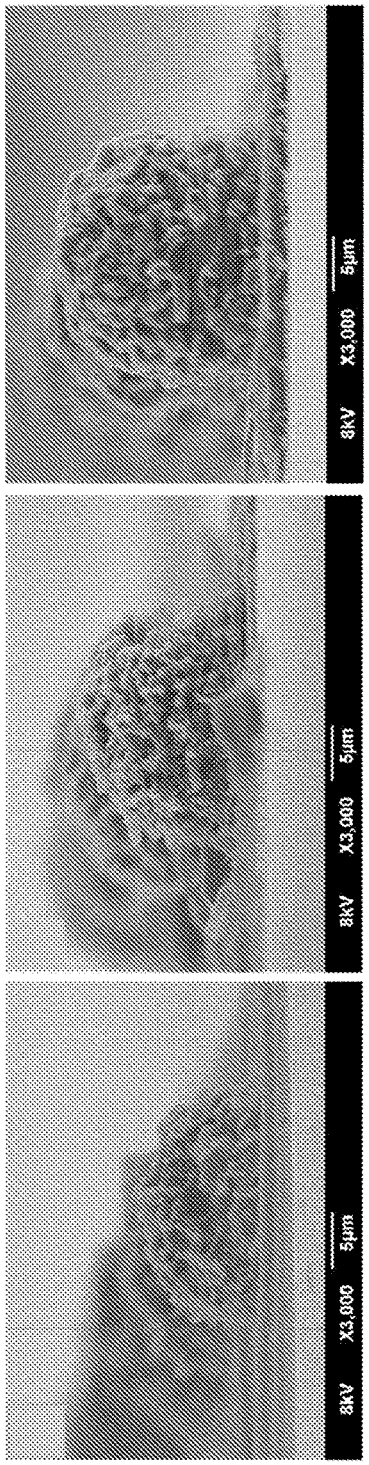
FIG. 17I
FIG. 17H
FIG. 17G
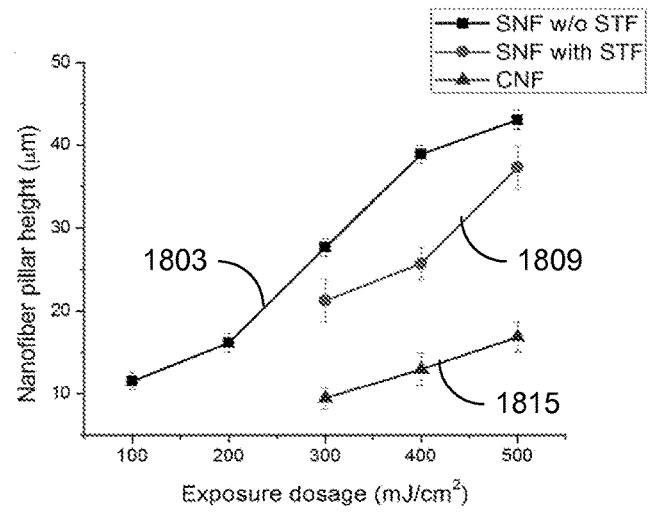
FIG. 18A
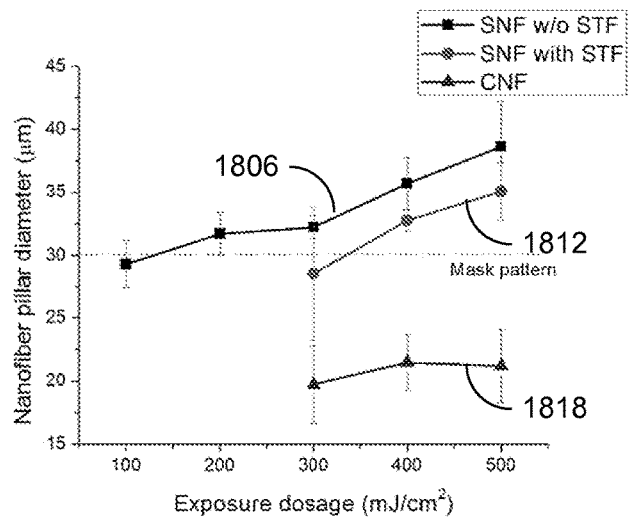
FIG. 18B

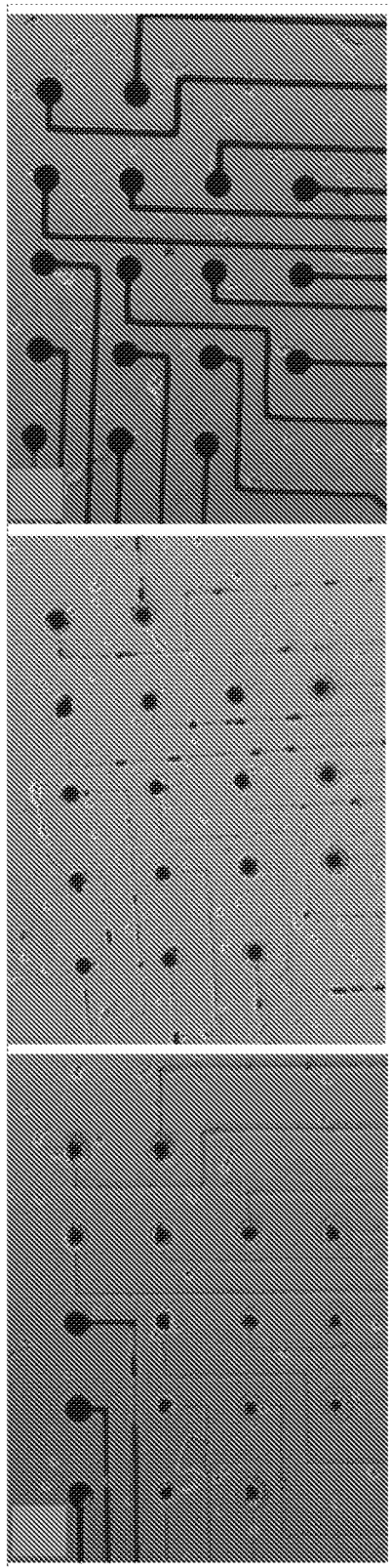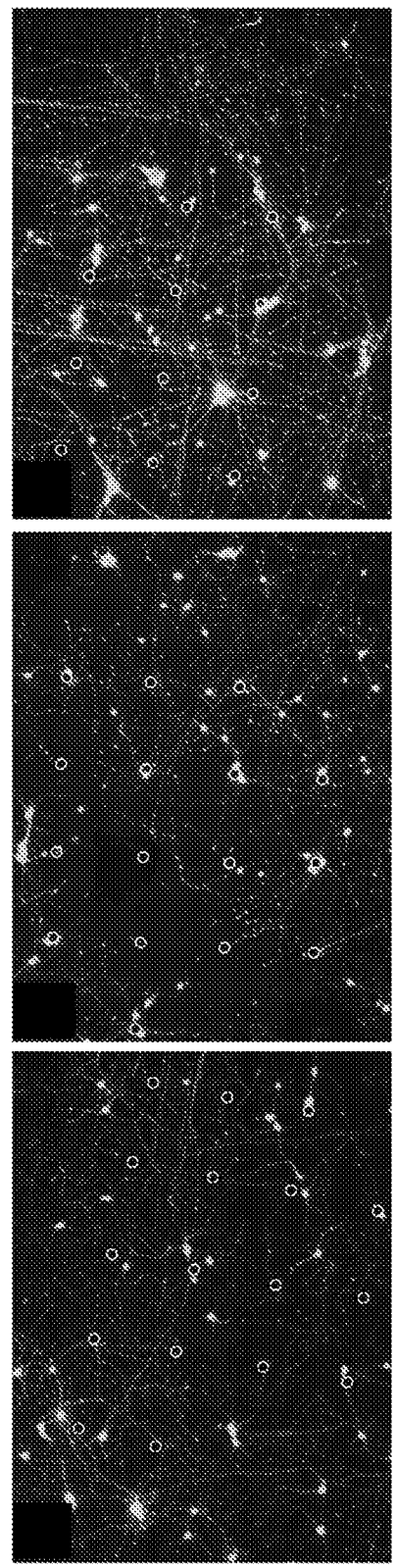
FIG. 19A FIG. 19B FIG. 19C FIG. 19D FIG. 19E FIG. 19F

NANOFIBROUS CARBON MICROSTRUCTURES

CROSS REFERENCE TO RELATED APPLICATIONS

This application is the 35 U.S.C. § 371 national stage application of PCT Application No. PCT/us2015/024141, filed Apr. 2, 2015, which claims priority to, and the benefit of, U.S. provisional application entitled "NANOFIBROUS CARBON MICROSTRUCTURES" having Ser. No. 61/975,451, filed Apr. 4, 2014, both of which are hereby incorporated by reference in their entirety.

STATEMENT REGARDING FEDERALLY SPONSORED RESEARCH OR DEVELOPMENT

This invention was made with government support under agreement ECCS-1132413 awarded by the National Science Foundation. The Government has certain rights in the invention.

BACKGROUND

Microelectrode arrays (MEAs) are used in various fields such as neural coding and decoding, recording field potentials for electrophysiology, multisite electroretinogram of explanted retinas, analysis of networks and cells in hippocampus brain slices and biorhythmic reading from cardiac myocytes. The primary function for MEAs is stimulation of electric current and/or recording bioelectric signal from biological tissues or cells.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 3A and 3B are scanning electron microscope (SEM) images of lithographically patterned nanofiber pillar structures, in accordance with various embodiments of the present disclosure.

FIGS. 4A-4C are graphical representations illustrating an example of oil immersion patterning of electrospun nanofibers, in accordance with various embodiments of the present disclosure.

FIGS. 6A-6F and 7A-7C are SEM images of examples of exposed nanofiber pillars in air and oil mediums with various exposure dosages, in accordance with various embodiments of the present disclosure.

FIGS. 12A and 12B are SEM images of lithographically patterned nanofiber pillar structures, in accordance with various embodiments of the present disclosure.

FIG. 13 is a graphical representation of a carbon nanofiber microelectrode array, in accordance with various embodiments of the present disclosure.

FIGS. 15A and 15B are graphical representations of optical simulation results for the diffraction effect on UV light by electrospun nanofibers in air and oil mediums, in accordance with various embodiments of the present disclosure.

FIGS. 15C-15D, 16A-16D and 17A-17F are SEM images of lithographically patterned nanofiber pillar structures, in accordance with various embodiments of the present disclosure.

FIGS. 16E-16F and 17G-17I are SEM images of the patterned nanofiber pillar structures of FIGS. 16C-16D and 17D-17F after carbonization, in accordance with various embodiments of the present disclosure.

FIGS. 18A and 18B are plots illustrating effects on height and diameter to exposure levels and carbonization of electrospun nanofibers without and with a thin film trace, in accordance with various embodiments of the present disclosure.

FIGS. 19A-19F are images of cultures of E18 rat neurons on fabricated nanofiber MEAs, in accordance with various embodiments of the present disclosure.

DETAILED DESCRIPTION

Figure 1A:
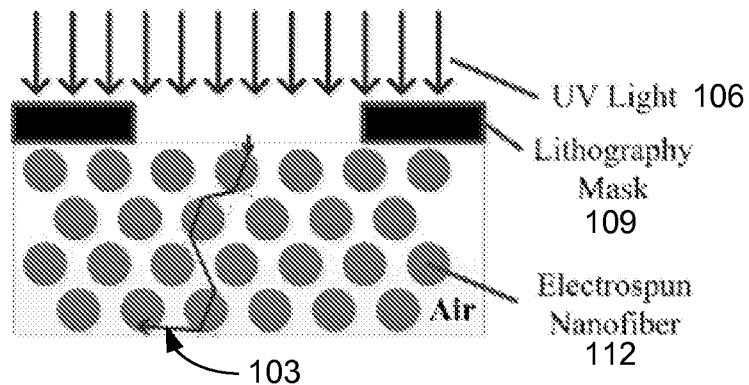
FIGS. 1A and 1B are graphical representations of examples of Fresnel-Huygens diffraction by electrospun nanofibers in air and oil mediums, respectively, in accordance with various embodiments of the present disclosure.

Disclosed herein are various examples related to nanofibrous three-dimensional (3D) microstructures including carbon nanofibrous microelectrode arrays. A fabrication process for 3D microstructures made of electrospun SU-8 nanofibers is discussed. The use of immersion lithography facilitates fabrication of high aspect ratio nanofiber pillars for various uses such as nanofiber microelectrode arrays. Reference will now be made in detail to the description of the embodiments as illustrated in the drawings, wherein like reference numbers indicate like parts throughout the several views.

A variety of applications including in-vivo cell incubators, tissue scaffolds, energy storage devices, and filtration systems utilize electrospun nanofibers. In many of the applications, spatial separation of microstructures in both lateral and vertical dimensions may be needed. For example, micro total analysis systems (μTAS) can use microsections of electrospun nanofibers to mimic bio-inspired architectures for spatio-temporal cell-cultures. If the electrospun nanofibers are made of a photosensitive polymer, then ultraviolet (UV) lithography may be used to replicate patterns in the photosensitive polymer in dimensions from millimeters and micrometers down to sub-micrometers. Photosensitive polymers that can be patterned include, but are not limited to, photosensitive polyimide, poly(methyl methacrylate) (PMMA), poly(methyl glutarimide) (PMGI), phenol formaldehyde resin (DNQ/Novolac) and commercial photoresist products such as AZ 4620, AZ 4562, Shipley 1400 series, Shipley 1800 series, and/or Futurrex NR series.

In an inhomogeneous medium such, diffraction and scattering effects of the optical ray trace can adversely affect the patterning of the material. Vertical limitations in patterning of electrospun nanofibers can be attributed to the diffraction and scattering effects of the optical ray trace in an inhomogeneous medium. When the characteristic dimension of a material of the medium is in a range similar to the wavelength of the optical light source and the medium includes a large refractive index difference between materials, poor directivity can result from amplification of the diffraction and scattering effects. For electospun nanofibers, the wavelength of the UV light source (e.g., an i-line of 365 nm, an h-line of 405 nm, and a g-line of 436 nm) is within the typical range of the nanofiber diameters (between 100 nm and 500 nm) and the refractive index difference between air and the polymer electrospun nanofibers is significant. Referring to FIG. 1A, shown is an example of Fresnel-Huygens diffraction by electrospun nanofibers in an air medium. As illustrated by the optical ray trace 103, UV light 106 passing through the lithography mask 109 is diffracted and scattered by the electrospun nanofibers 112. Because of the diffraction and scattering effects in an air environment, direct lithographical patterning of electrospun nanofibers may be limited to thicknesses of only a few micrometers, which are far smaller than the few hundred micrometers that are useful for many 3D biomedical, chemical, and electrical applications.

Figure 1B:
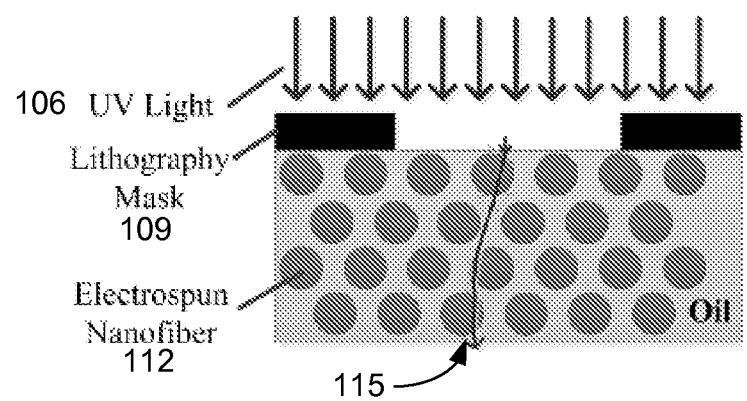

Patternability of nanofibrous 3D microstructures can be improved when carried out in a refractive index matching environment. When the electrospun nanofibers are in a refractive index matching material such as oil, the lithographic sensitivity can be greatly enhanced because the refractive index of the oil is closer to that of the polymer nanofibers. Referring to FIG. 1B, shown is an example of Fresnel-Huygens diffraction by electrospun nanofibers in an oil medium. Because the difference in refractive index is reduced, the diffraction and scattering of the UV light 106 passing through the lithography mask 109 is reduced as illustrated by the optical ray trace 115, allowing thicker layers of electrospun nanofibers 112 to be patterned. Numerical analysis using the Fresnel-Huygens diffraction principle in wave propagation shows a decrease in ray scattering in the oil medium of FIG. 1B compared to that of the air medium of FIG. 1A. Refractive index matching materials can include, but are not limited to, industrial grade lubricants, silicone oils, vegetable oils, and/or other refractive index matching liquids (e.g., refractive index matching liquids from Cargille Labs).

Figure 2A:
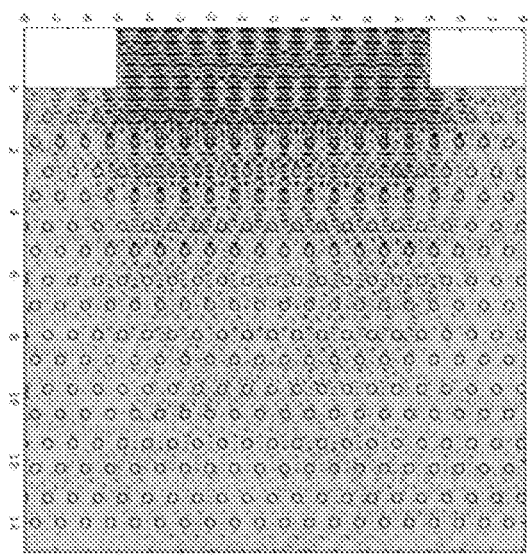
FIGS. 2A and 2B are graphical representations of optical simulation results for the diffraction effect on UV light by electrospun nanofibers in air and oil mediums of FIGS. 1A and 1B, in accordance with various embodiments of the present disclosure.
Figure 2B:
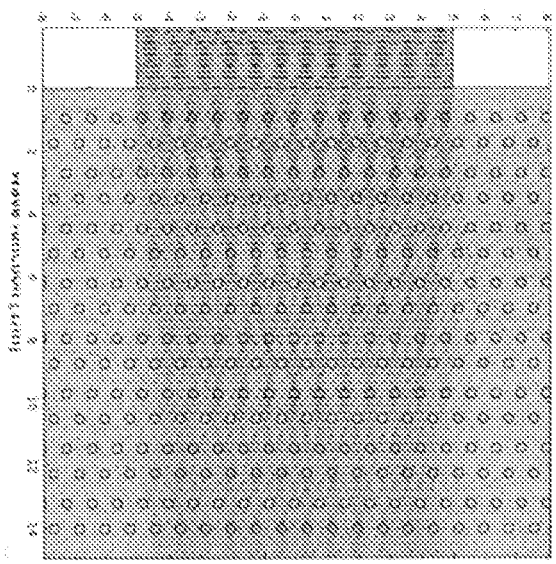

FIGS. 2A and 2B are plots of optical simulation results using COMSOL Multiphysics (COMSOL Inc.) showing the diffraction effect on UV light 106 with electrospun nanofibers 112 in the air medium of FIG. 1A and the oil medium of FIG. 1B, respectively. In FIG. 2A, the light dispersion with air is mainly due to the large difference in the refractive index (n) between that of the air ($n_{air}$=1) and the polymer ($n_{SU-8}$=1.67). With the higher refractive index of oil ($n_{oil}$=1.47) in FIG. 2B, the reduced mismatch in the refractive indices minimizes the overall diffraction effect, thus mimicking that of a homogeneous polymer medium. The smaller mismatch between refractive indices allows the UV light 106 to penetrate further into the layer of electrospun nanofibers 112, resulting in taller structures being produced with higher aspect ratios.

Referring to FIGS. 3A and 3B, shown are scanning electron microscope (SEM) images of lithographically patterned 60 μm diameter pillar structures fabricated using electrospun photosensitive epoxy, e.g. SU-8 nanofibers (Microchem, Inc.), in an air medium and an oil medium, respectively. Using the same exposure dosage of 400 mJ/cm$^2$ for both mediums, the pillar 303 fabricated in air is 25.9±4.1 μm tall and 100.8±24.0 μm in diameter, while the pillar 306 fabricated in oil is 55.5±3.3 μm tall and 73.3±5.8 μm in diameter. While the pillar 303 fabricated in air exhibits a convex lens architecture, the pillar 306 fabricated in oil results in a higher aspect ratio pillar due to the minimization of light diffusion during the exposure phase.

Figure 4D:
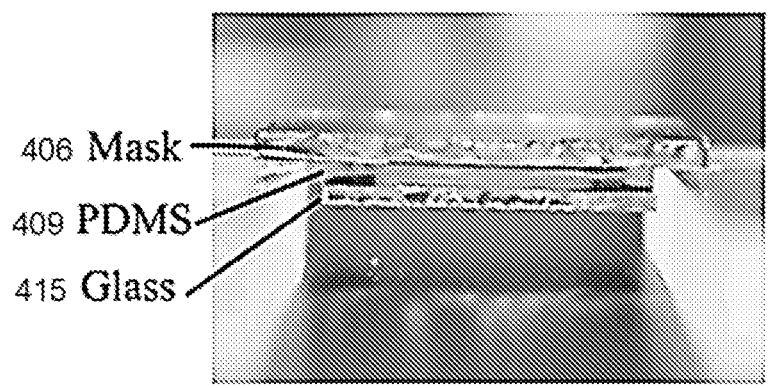
FIG. 4D is an image of an example of a setup for oil immersion lithography of electrospun nanofibers, in accordance with various embodiments of the present disclosure.

An example of a fabrication process for in-situ patterning of electrospun nanofibers on a lithographic mask is shown in FIGS. 4A-4C. Initially, SU-8 nanofibers 403 are electrospun from a solution of SU-8 (e.g., SU-8 in N,N-Dimethylformamide (DMF) at 60.9 wt %) on a pre-patterned chrome photomask 406 as illustrated in FIG. 4A. A polydimethylsiloxane (PDMS) membrane 409 can be used to form a reservoir around the periphery of the nanofibers 403. The reservoir is then filled with oil 412 (e.g., Wesson canola oil, ConAgra Foods Inc.) to submerge the nanofibers 403 as illustrated in FIG. 4B. The setup can be placed under vacuum (e.g., overnight) to degas it. The reservoir is then covered with a cover glass 415 and flipped over for exposure of the nanofibers 403. As illustrated in FIG. 4C, the nanofibers 403 are exposed through the chrome photomask 406 by i-line UV light 418 (e.g., Orion Instruments, Inc.). The exposed area of the electrospun nanofibers 403 can be cross-linked by a post exposure bake on a hotplate (e.g., Echotherm HP40, Torrey Pines Scientific) or in a convection oven (e.g., Isotemp 281A, Fisher Scientific) and developed in SU-8 developer (e.g., Microchem Inc.) to remove both the unexposed SU-8 and the oil. FIG. 4D is an image of an implemented lithography setup of the oil immersed nanofibers for backside UV exposure shown in FIG. 4C. In some implementations, exposure of the photosensitive nanofibers can be through a front side photomask disposed adjacent to a side of the photosensitive nanofibers opposite the patterned substrate. For example, the cover glass 415 of FIG. 4C can be patterned with a front side photomask and the nanofibers 403 can be exposed through the front side photomask. Resolution of the resulting nanofiber pillars can be improved by positioning a pre-patterned front side photomask between the cover glass 415 and the nanofibers 403.

Figure 5A:
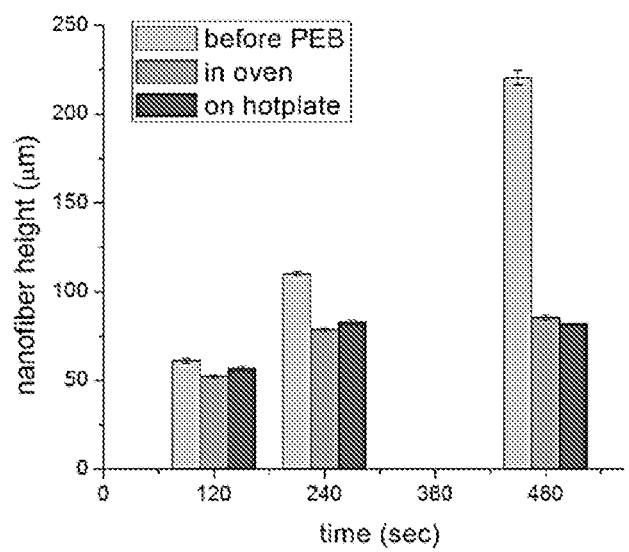
FIGS. 5A and 5B are plots illustrating the effect of post exposure bake on the height of the patterned electrospun nanofibers, in accordance with various embodiments of the present disclosure.
Figure 5B:
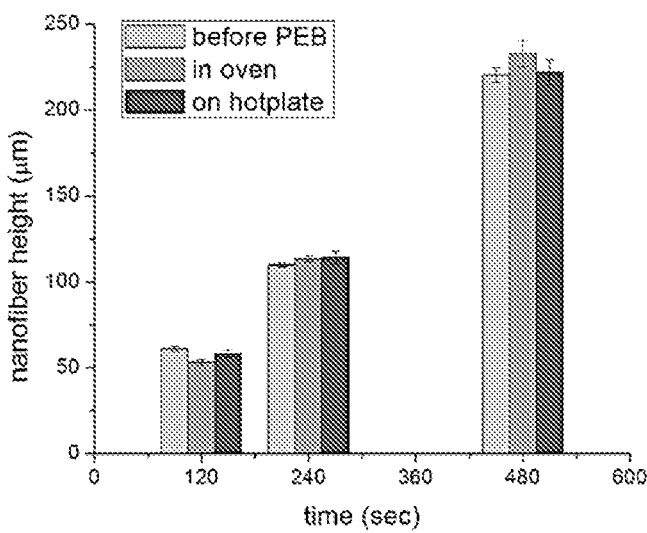

Wave propagation simulations (using COMSOL Multiphysics, Ver. 4.3) were performed using uniformly aligned fibers with a fiber diameter of 300 nm and a pitch of 600 nm. Each nanofiber layer was aligned with the x-axis or y-axis in an alternating fashion, and the incoming wavelength was fixed at 365 nm. Topographical measurements were performed using a surface profiler tool (e.g., Dektak 150, Bruker Co.) and the measured data were analyzed using statistical data analysis software (e.g., OriginPro 8, OriginLab Co.). FIGS. 5A and 5B show plots of membrane height versus electrospinning time for exposed nanofibers before post exposure bake (PEB). FIG. 5A illustrates the reduction in membrane height after PEB in an oven and on a hotplate, when in an air medium and FIG. 5B illustrates the change in membrane height after PEB in the oven and on the hotplate, when in an oil medium. Error bars of the nanofiber heights are plotted using a 95% conformance interval and calculated using 2-tail student's t-distribution. Nanofiber morphology was characterized using image analysis (e.g., ImageJ software) of SEM images (using JEOL 5700, Jeol Co.). Linear fitting for the swing curves to determine contrast ratio was performed using a least square method in OriginLab.

As can be seen in FIGS. 5A and 5B, thickness of the nanofiber stack increases with increasing electrospinning time. The cross-linking of the SU-8 nanofibers depends on the exposure dosage and the thermal energy in the post exposure step, following the release of Lewis acid. To differentiate the effect of thermal heat transfer with that of the exposure dosage, samples, which were collected using different electrospinning times, were over exposed using the same exposure dosage of 2000 mJ/cm² and post-exposure baked (PEB) using both a hot plate and convection oven. In FIG. 5A, the height of the nanofibers decreased following the PEB of nanofibers exposed in the air medium. The decrease in height was observed for both the hot plate and convection oven samples and the height saturates at around 75 μm even though the height of the pre-PEB fibers are over 200 μm. In the case of oil medium exposed nanofibers illustrated in FIG. 5B, the height of the nanofibers remains approximately the same following the PEB. The height of the nanofibers is independent of use of the hot plate or the convection oven, although the slight differences in height that were observed may be attributed to sample to sample deviations. Therefore, the decrease in height of nanofibers in the air medium following the PEB was not due to inadequate transfer of thermal energy.

To verify the effect of the air and oil mediums on the height of patterned nanofibers, groups of unexposed nanofibers were collected over 6 minutes of electrospinning time and exposed with increasing dosages of UV light using an array of circular patterns with 60 μm diameter and 200 μm pitch. FIGS. 6A-6C are images of examples of exposed nanofibers in air with exposure dosages of 200 mJ/cm², 300 mJ/cm², and 400 mJ/cm², respectively. In air, the height of the 3D microstructures reaches approximately 30 μm but the diameter increases to 1.68 times the mask diameter at 400 mJ/cm². FIGS. 6D-6F are images of examples of exposed nanofibers in oil with exposure dosages of 200 mJ/cm², 300 mJ/cm², and 400 mJ/cm², respectively. In contrast to air, the oil medium demonstrates an increasing nanofiber height with increasing exposure dosage. At 400 mJ/cm², the oil medium resulted in an increase of 2.14 times the microstructure height in air, while the diameter only increased to 1.2 times the 60 μm mask diameter. Comparison of FIGS. 6A-6C to FIGS. 6D-6F illustrates the reduction in diffraction when the nanofibers are immersed in an oil medium. These images demonstrate the effects of the reduced diffraction with oil immersion lithography, which gives a laterally increased height of 3D nanofiber microstructures.

Figures 7A, 7B, 7C:
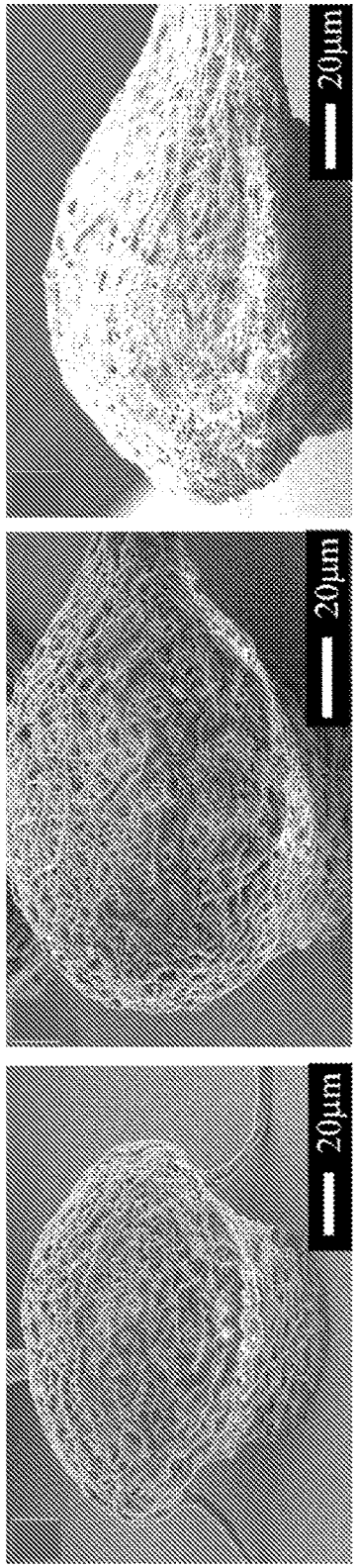

FIGS. 7A-7C show examples of 60 μm circular patterns that were exposed with dosages of 450 mJ/cm², 600 mJ/cm² and 900 mJ/cm², respectively. The increased exposure dosage of the nanofiber pillar arrays demonstrated the formation of bridging structures between adjacent pillars. Not only did the diameter at the base of the pillars increase, but nanofibers also extended from the top of the pillars to adjacent pillars to form canopy type overhanging bridges. The bridging effect may be attributed to the proximity of adjacent pillars, where the sum of partial dosages from adjacent pillars is sufficient to cross-link the nanofibers. As the dosage was increased from 600 mJ/cm² to 900 mJ/cm², the width of the resulting bridges increased such that at 900 mJ/cm², all the fibers are cross-linked on the top. The lateral diffusion of UV light with increasing exposure dosage is better explained with the help of the Fresnel diffraction principle.

Photoresist films in UV lithography suffer from pattern distortion due to optical diffraction. The farther the UV light travels from the mask and polymer interface, the more diffraction effect results. The diffraction effect becomes more significant when the structural dimension of the polymer nanofibers is in a similar range as the wavelength of the UV light source (about 300 nm to about 400 nm). As a diffraction model, the Huygens-Fresnel principle uses the Kirchhoff boundary conditions for the near field and Sommerfeld radiation approximation for the far field boundary conditions. In solving the time harmonic propagation of light using the Helmholtz equation, the scalar potential U can be solved to get the accumulated light intensity at a given point in the photoresist given by $I(P_0)$ as shown in EQNS. (1) and (2). The exposure dose received at the nanofibers is given by the accumulated light intensities at any given position in the photoresist and is defined by D, which is a function of the position ($P_0$) and exposure time ($t_{exp}$) as shown in EQN. (3):

$$-\nabla \cdot (\Delta U) - k^2 U = 0; k = \frac{2\pi n}{\lambda} \quad (1)$$

$$I(P_0) = \frac{c\epsilon}{2}|U(P_0)|^2 \quad (2)$$

$$D(P_0, t_{exp}) = \frac{(1-R_1)I(P_0)t_{exp}(e^{-\alpha_{unexp}z} - e^{-\alpha_{exp}z})}{(\alpha_{unexp} - \alpha_{exp})z} \quad (3)$$

where U is the scalar function, k, n and ε are the wave number, refractive index and dielectric constant of the medium, respectively, and c and λ are the velocity and wavelength of the UV light, respectively. $R_1$ is the reflection coefficient at the glass/oil interface, z is the lateral distance from mask to position $P_0$, and $\alpha_{exp}$ and $\alpha_{unexp}$ are the absorption coefficient of exposed and unexposed SU-8, respectively.

Figure 8A:
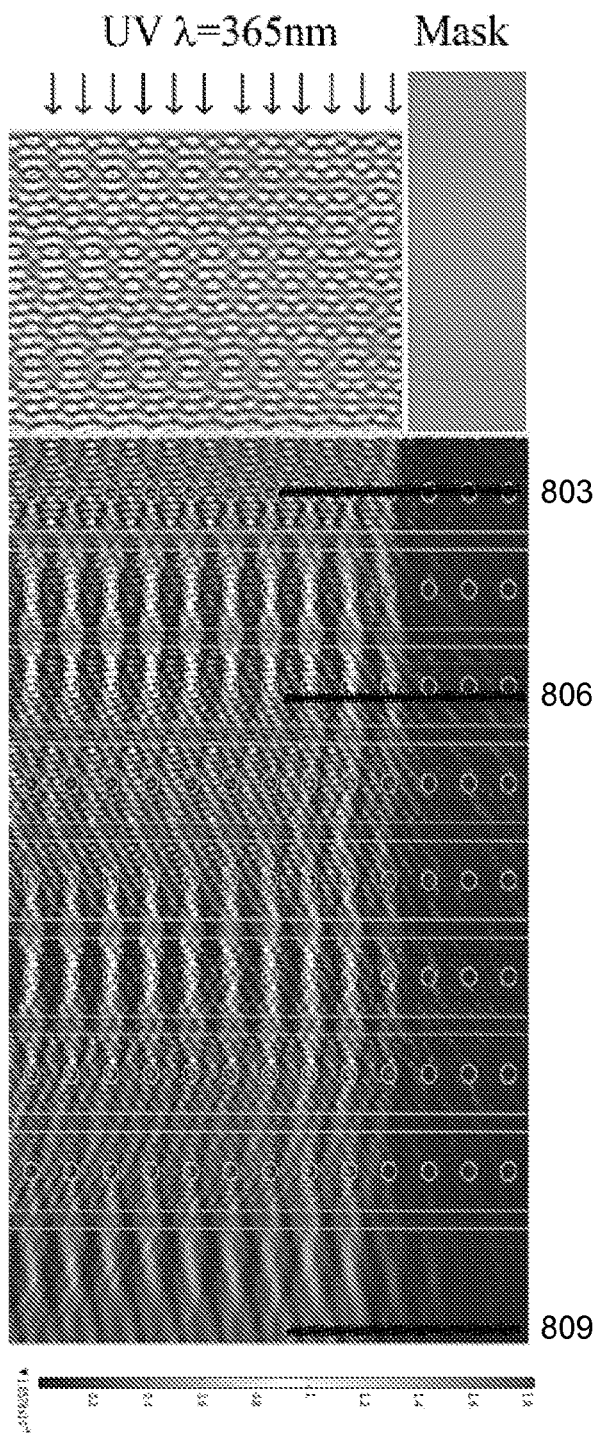
FIG. 8A is a graphical representation of an example of normalized dosage distribution of UV light directed through nanofibers in an oil medium by a mask, in accordance with various embodiments of the present disclosure.
Figure 8B:
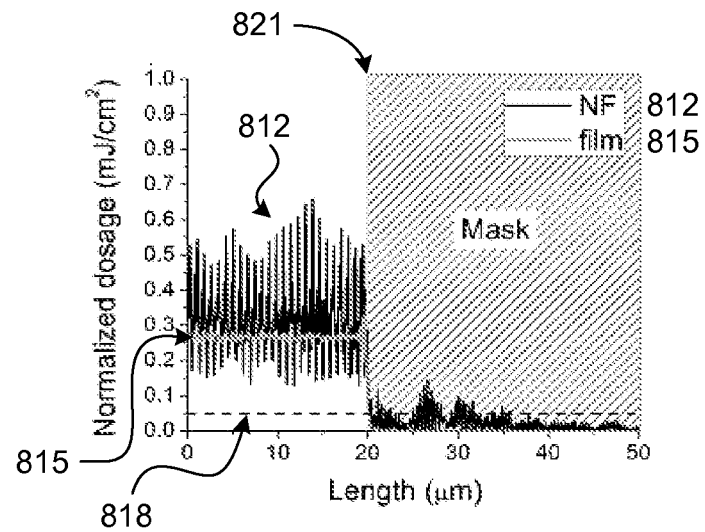
FIGS. 8B-8D are plots illustrating optical intensity distributions at the near-field, mid-field, and far-field locations in the nanofibers of FIG. 8A, in accordance with various embodiments of the present disclosure.
Figure 8C:
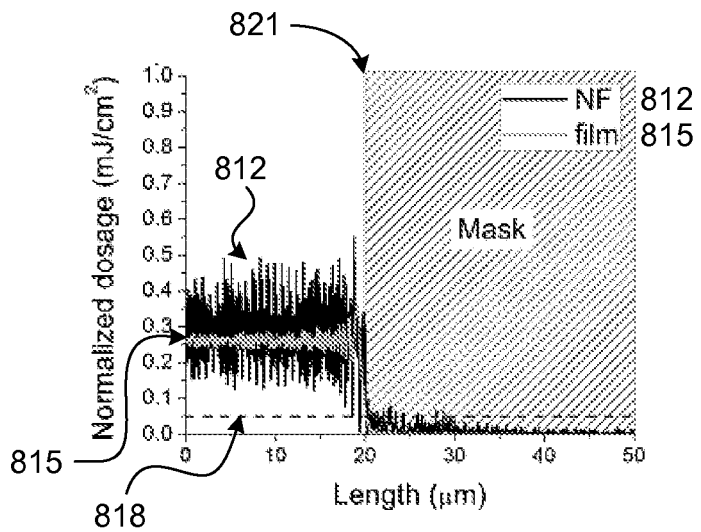
Figure 8D:
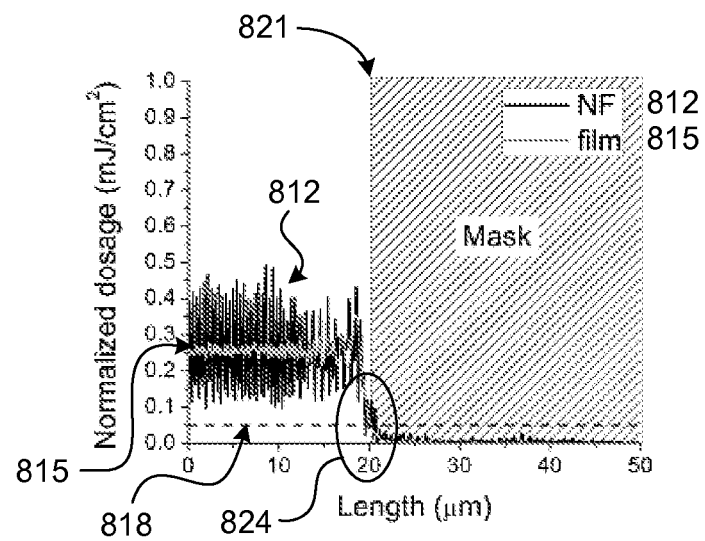

Referring to FIGS. 8A-8D, shown is an example of diffraction in an inhomogeneous nanofibrous medium. The spatial distribution of the normalized dosage was calculated using EQNS. (1) and (2) when the medium consists of nanofibers and oil. The nanofibers were modeled as uniformly aligned fibers with a fiber diameter of 300 nm and a pitch of 600 nm. Each nanofiber layer was alternatingly aligned in the x-axis or y-axis as illustrated by the layers of lines and circles. FIG. 8A shows the normalized dosage distribution of UV light (λ=365 nm) directed through the nanofibers in an oil medium by a mask. FIGS. 8B-8C show the optical intensity distributions along the indicated lines at the near-field 803, mid-field 806, and far-field 809 locations in FIG. 8A, respectively. The normalized dosage distribution at the nanofiber in the oil medium (NF 812) is compared with that of the homogeneous SU-8 polymer film (film 815). The dashed line 818 indicates the threshold dosage for SU-8, which indicates exposure dosage sufficient to cross-link. In the case of near-field at z=0.4 μm from the mask (FIG. 8B), while the cross-linked area of the SU-8 film is clearly demarcated at the mask boundary 821, the normalized dosage distribution at the nanofiber 812 shows that nanofibers under the mask have areas that are being cross-linked. In the case of mid-field (FIG. 8C), with the exposure dosage decreased when compared to the near-field (FIG. 8B), the nanofibers under the mask pattern are not cross-linked. The film 812 and nanofibers 815 under the open window of the mask still receive more than the threshold dosage 818 and are thus cross-linked. In the case of far-field at z=15 μm (FIG. 8D), both the SU-8 thin film 815 and the nanofibers 812 observe a decrease in the expose dosage, with some areas 824 under the open windows of the mask receiving dosage less than the threshold dosage.

Figures 9A, 9B, 9C:
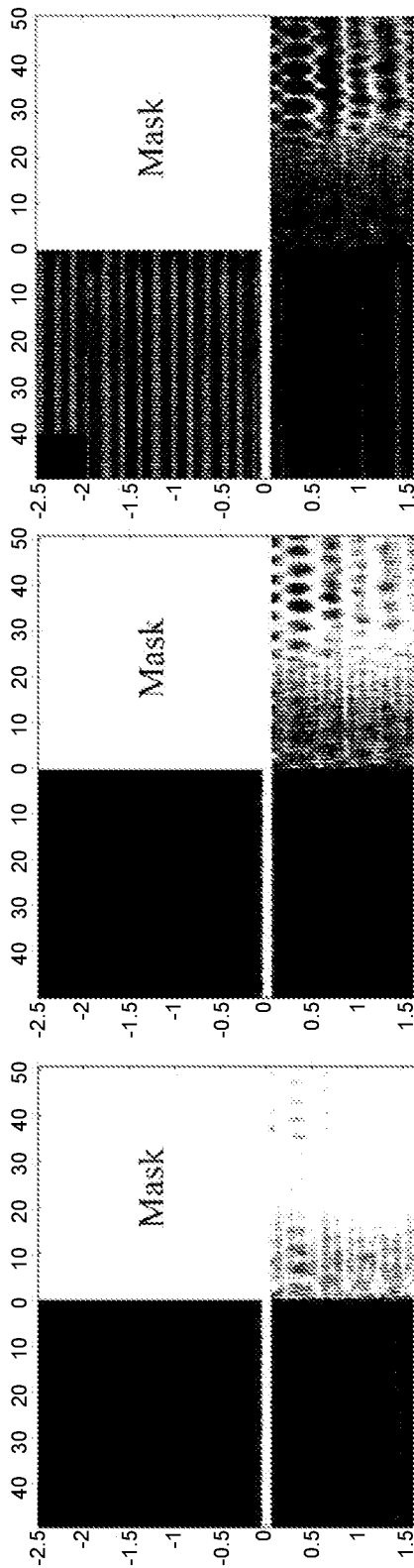
FIGS. 9A-9C are graphical representations illustrating examples of cross-linking of electrospun nanofibers around a mask interface with various doses of UV light, in accordance with various embodiments of the present disclosure.

As the optical dose increases, the diffraction effect becomes significant. In order to visualize the diffraction effect in the photoresist around the edge of the masked area and the exposed area, every point in the photoresist which receives a dosage above the intrinsic UV sensitivity of SU-8 were mapped black. FIGS. 9A-9C show a series of mapped cross-sectional profiles around the nanofiber and mask interface with increasing dosage calculated using EQNS. (2) and (3). In the simulated resist profiles, dark (black) areas in the medium indicate cross-linked polymer and light (white) areas denote that of uncross-linked polymer with exposure dosages of (a) 120 mJ/cm² for FIG. 9A, (b) 240 mJ/cm² for FIG. 9B, and (c) 1200 mJ/cm² for FIG. 9C. With increasing dosage, there is an increase of the dark area in the lateral direction, which indicates the wider polymerized patterns. While the profile boundaries cannot be clearly demarcated, patterns that delineate the exposed from the unexposed can be qualified.

Figures 10A, 10B, 10C:
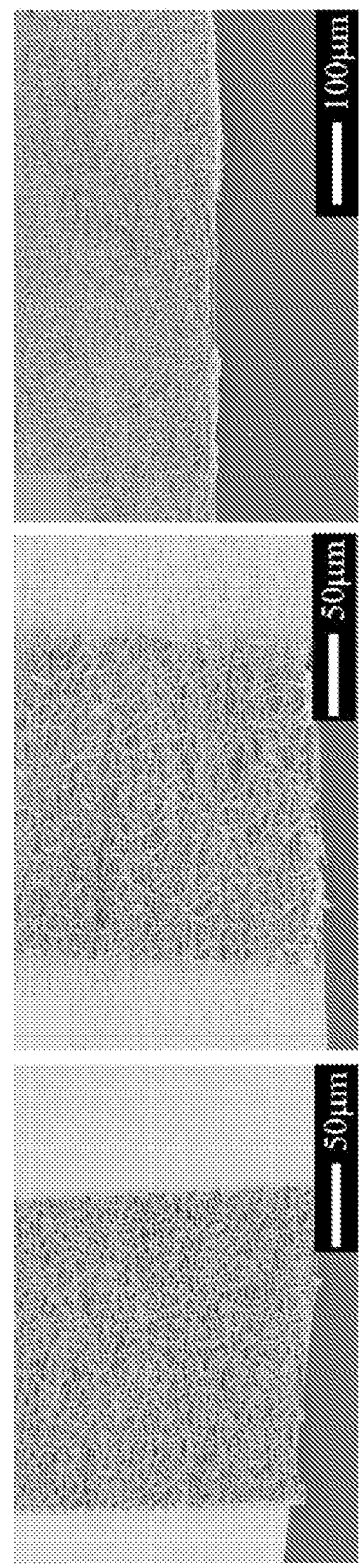
FIGS. 10A-10C are images of examples of cross-linking of electrospun nanofibers around a mask interface at the various doses of UV light of FIGS. 9A-9C, in accordance with various embodiments of the present disclosure.

FIGS. 10A-10C show UV lithographically patterned nanofibrous membrane stacks with a pattern width of 200 μm and a stack thickness of 10 μm as a function of the optical dosage $D_o$ of (a) 120 mJ/cm², (b) 240 mJ/cm², and (c) 1200 mJ/cm², respectively. In FIG. 9A, the demarcated regions of the exposed and unexposed nanofibers are clearly observed similar to those in FIG. 10A. With an increased optical dosage in FIG. 10B, a scattered thin layer of nanofibers is observed on the substrate under the masked area, which corresponds to the dotted regions on the mask-nanofiber interface in FIG. 9B. The irregular cross-linking of nanofibers under the mask is insufficient to bind the layer in a full thickness, resulting in the scattered residual nanofibers. FIG. 10C shows the fabricated structure with an overexposure dosage of $D_o$=1200 mJ/cm², where a large portion of the nanofibers under the masked area is cross-linked. Note that the laterally extended areas from both edges of the mask patterns are overlapped and there is almost no distinction between the masked and unmasked areas, which is consistent with that observed in FIG. 9C.

For the quantitative analysis of patterned nanofiber stacks, the resist sensitivity or exposure response curves are plotted of nanofiber heights with increasing exposure dosage. Resist contrast ratio is determined by the positive slope of the linear growth region of the sensitivity curve. The higher the contrast ratio $\gamma_n$, the higher is the resolution capability of the resist, in this case, the medium of optical transmission.

$$\gamma_n = \frac{1}{\log D_g^o - \log D_g^i} \quad (4)$$

where $D_g^o$ is the dosage required to reach saturation and $D_g^1$ is the critical dosage minimally required to crosslink the photoresist.

Figure 11A:
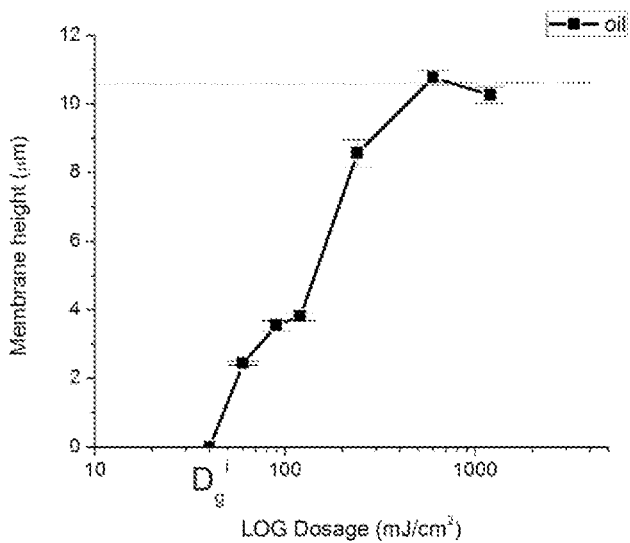
FIGS. 11A-11C are plots of experimental results illustrating various effects of exposure of nanofiber stacks in air and oil mediums, in accordance with various embodiments of the present disclosure.
Figure 11B:
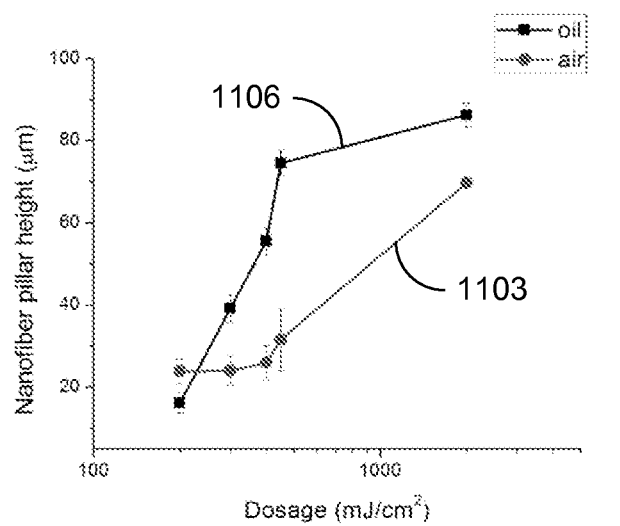
Figure 11C:
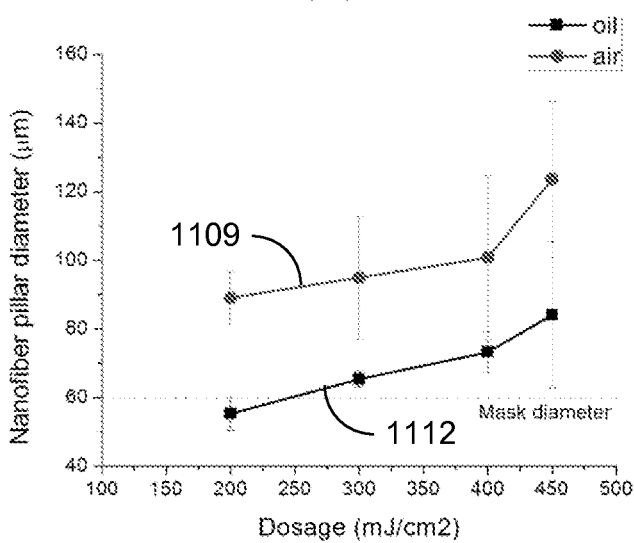

FIG. 11A shows the experimental results of the nanofiber stack with an unexposed thickness of 10 μm. The nanofiber height is plotted against exposure dosage with an oil medium. The critical dosage $D_g^i$ of SU-8 nanofiber stacks was experimentally determined to be between 45 mJ/cm² and 55 mJ/cm², which matches well with that of SU-8 solid thin film. Increasing the dosage increases the height of the developed nanofibers until it saturates at the intrinsic height of the unexposed electrospun nanofiber stack. FIG. 11B shows the resist swing curves of 80 μm electrospun nanofiber stacks exposed in both air (curve 1103) and oil (curve 1106) mediums and FIG. 11C shows the effect of the exposure dosage on pillar diameter in air (curve 1109) and oil (curve 1112). In the case of the air medium (curve 1103), the diffraction effect severely limits the transmission of dosage through the bulk of the nanofibers and the patterned nanofibers gradually increases to a height of 69.7±0.7 μm at 2000 mJ/cm². While in the case of oil medium (curve 1106), the nanofiber height reaches 74.5±3.0 μm at only 450 mJ/cm².

From the swing curves of FIG. 11B, the slope of the increasing nanofiber height intersecting with maximum possible height of nanofibers are used to determine the saturation dosage $D_g^O$, which is 3100 mJ/cm² and 550 mJ/cm² for air and oil mediums, respectively. Using EQN. (4), the contrast ratio can be calculated for air and oil to be $\gamma_{n\_air}$=0.56 and $\gamma_{n\_oil}$=0.96, respectively. At 450 mJ/cm² in air, the height and diameter of nanofiber is 31.5±7.8 μm (curve 1103) and 123.6±22.8 μm (curve 1109), respectively, which gives an aspect ratio of 0.26. By contrast, in the oil medium the height and diameter of nanofiber is 74.5±3.1 μm (curve 1106) and 84.1±21.4 μm (curve 1112), respectively, which gives an aspect ratio of 0.89. Thus, the use of an oil medium not only allows higher aspect ratio structures but also improves the pattern resolution in SU-8 nanofiber stacks. For example, the aspect ratio for a structure generated in an oil medium may be greater than and/or equal to 0.3, greater than and/or equal to 0.4, greater than and/or equal to 0.5, greater than and/or equal to 0.6, greater than and/or equal to 0.7, greater than and/or equal to 0.8, greater than and/or equal to 0.9, and/or larger.

Nanofiber pillar arrays can be fabricated using oil immersion lithography for use as high aspect ratio carbon nanofibrous microelectrode arrays (CNF-MEAs) with high resolution. FIGS. 12A and 12B are images of examples of 3D nanofibrous microstructures fabricated using oil immersion lithography. FIG. 12A shows an example of a micropillar array fabricated using single backside exposure of 900 mJ/cm² and FIG. 12B shows a magnified view of a row of pillars in FIG. 12A. During fabrication of the nanofibrous 3D microelectrodes, oil immersion can negate diffraction effects intrinsic to the photopatterning of electrospun nanofibers to give increased aspect ratio microarchitectures. Nanofiber electrode resistivity was characterized and its performance was compared to that of carbon thin film. In vitro testing of electrodes was also performed using E18 cortical neurons and analyzed for cell density and cell viability.

Microelectrode arrays (MEAs) can be used for stimulating and receiving electrical signals between human and machines and for in vitro neural study. Unlike microelectrode probes, microelectrode arrays are planar architectures with non-invasive electrodes that can be used to measure the distributed electrical sensitivity of neural networks while still having the resolution of a single neuron. MEAs can be biocompatible to support tissue growth as well as exhibit low impedance (500 kΩ at 1 kHz) to measure the small signals (about 10 μV to about 100 μV) of the neurons. Earlier generations of MEAs were fabricated on glass substrates with patterned gold or indium tin oxide as conductors between the electrodes and read out probes. The electrodes were electroplated porous platinum (Pt black), followed by the addition of a biocompatible insulation layer. Porous conductive electrodes can be used to enhance surface area for higher interface capacitance, thereby reducing recording impedance. High surface area electrodes not only decrease the electrical impedance but also enhance interactions with cultured neurons. But Pt black may not be durable for long term culturing and can be replaced by mechanically stronger and electrically superior material such as iridium oxide or titanium nitride.

Other conductive polymers can also be electroplated such as polypyrrole (PPy), polythiopene (PT), polyaniline (PAni) and poly(3,4-ethylenedioxythiopene) (PEDOT). In addition to being a stable conductive polymer layer, they can also function as a molecular counter-ion responsible for healthy tissue culture. To form porous PEDOT layers, polystyrene beads can be used as a template in the electrodeposition process on neural probes and then etched in toluene. Another electrode material that can be used is chemically vapor deposited carbon nanotube (CNT) forests which have demonstrated high conductivity and a large double layer capacitance inherent with large surface area. But the free standing CNT forests may be fragile and can be mechanically reinforced either with thermal oxide or electroplated PPy. Anodized aluminum oxide layers with their high aspect ratio pores can also be used to enhance the surface area of patterned electrodes and high frequency action potentials on cultured HL-1 cells.

The fabrication process of high aspect ratio carbon nanofiber microelectrode array will be described herein using electrospun nanofibers, immersion photolithography, and carbonization. Referring to FIG. 13, shown is an example of a nanofiber based microelectrode array, where high aspect ratio carbon nanofiber pillars are the electrodes which interact with the test specimen and carbon thin film (CTF) are the trace electrodes which connect the nanofiber electrodes with the read out circuits. Oil immersion lithography has been exploited for high aspect ratio nanofiber pillars.

Figure 14A:
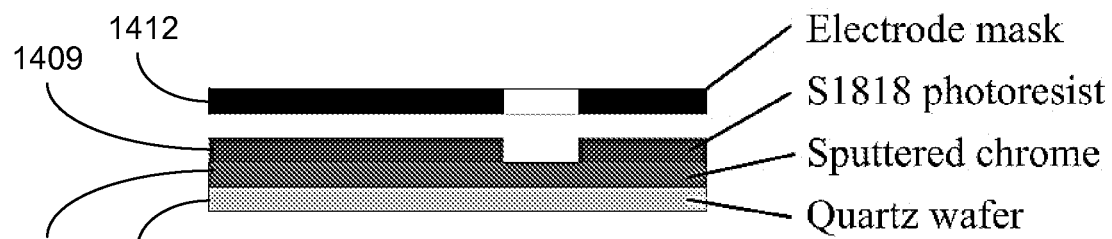
FIGS. 14A-14D are graphical representations illustrating an example of oil immersion patterning of electrospun nanofibers to form carbon nanofiber microelectrode arrays of FIG. 13, in accordance with various embodiments of the present disclosure.
Figure 14B:
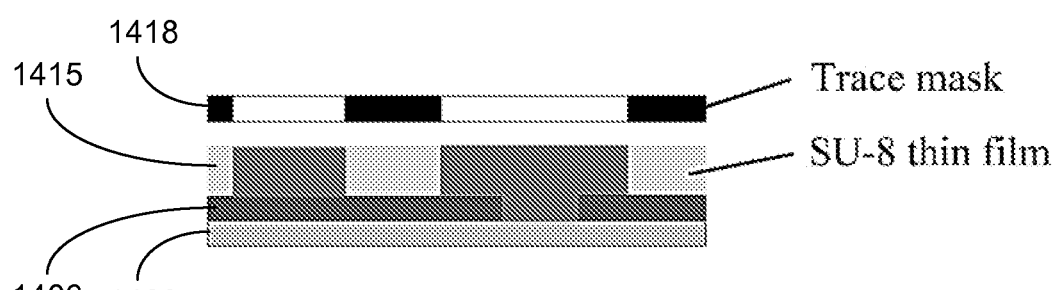

Referring to FIGS. 14A-14D, shown is an example of a fabrication process of the nanofiber pillar microelectrodes on a CTF trace using nanofiber immersion photolithography. First, a quartz substrate (or wafer) 1403 is sputtered with chrome 1406 (e.g., about 120 nm thin chrome layer) and patterned with positive resist 1409 (e.g., Shipley S1818) to give a photolithographic mask 1412 of the electrodes as shown in FIG. 14A. Second, an SU-8 thin film 1415 (e.g., about 7 μm thick SU-8) is spin coated on the quartz substrate 1403 and etched chrome 1406 and patterned with the trace patterns of the microelectrode array (defined by trace mask 1418) using, e.g., a Karl Suss MA6 aligner as shown in FIG. 14B.

Figure 14C:
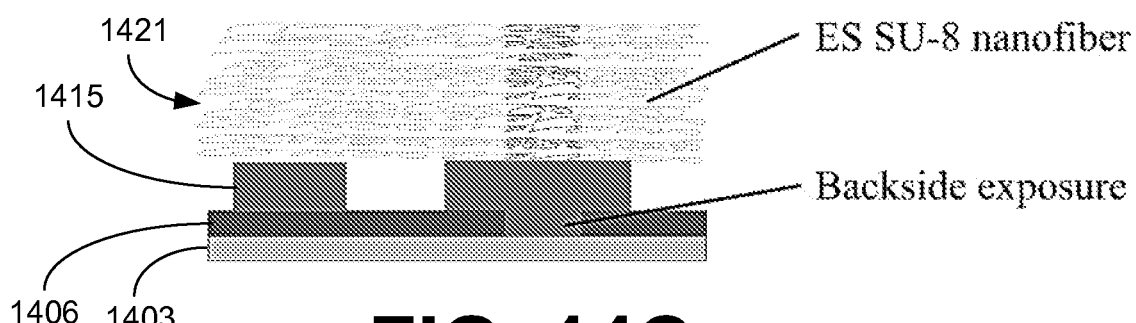
Figure 14D:
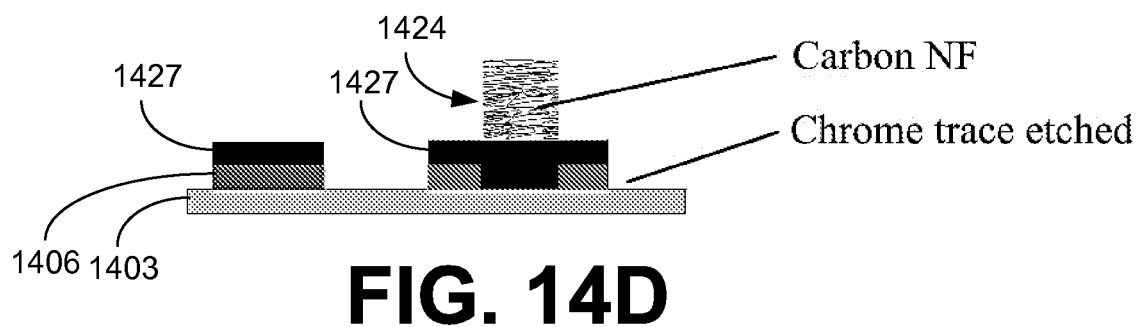

Third, SU-8 nanofibers 1421 are electrospun (e.g., from a 60.9 wt % solution with dimethylformamide) on the SU-8 thin film 1415 with an electric field of 1.5 kV/cm and a flow rate of 1 ml/min directly on the patterned quartz substrate as shown in FIG. 14C. A reservoir is formed around the nanofibers 1421, which are then immersed in an oil medium and exposed to UV light using the quartz wafer 1403 and sputtered chrome 1406 as the mask. The UV light exposure is followed by post exposure bake and developing steps. Fourth, the chrome layer 1406 is etched to electrically isolate the patterned SU-8 nanofibers (SNF) 1421 and SU-8 thin film (STF) 1415 trace patterns. Then, the MEAs are carbonized under a forming gas atmosphere (e.g., 4% hydrogen, BAL nitrogen) at a flow rate of 13 slm (standard liter per minute) with the final carbonization temperature reaching 1000° C. with a ramp rate of about 5° C./min to about 10° C./min as shown in FIG. 14D. The carbon nanofiber (CNF) pillars 1424 and carbon thin film (CTF) traces 1427 remain after developing.

Scanning electron microscope (SEM) (e.g., JEOL 5700) images were taken after sputtering a 20 nm chrome layer on the samples. Nanofiber pillar heights and diameters were measured from cross-sectional SEM images using ImageJ imaging software. Statistical distributions were plotted with 95% confidence intervals using a T distribution with N=5 and a 2-tailed distribution. A 7-day on vitro analysis on the fabricated MEAs was performed using E18 rat cortical neurons. The MEAs were treated with 0.1% polyethylenimine (w/v) for supporting long term cell growth. Cell growth was analyzed via calcein and AM staining.

Optical simulations of wave propagation in the nanofiber matrix were performed using the COMSOL Multiphysics tool. Huygen-Fresnel diffraction principles were applied to propagating wave functions to determine the accumulated UV light intensities. FIGS. 15A and 15B show intensity plots of UV light in the nanofiber matrix in air and oil media, respectively. While the air medium of FIG. 15A demonstrates an increased scalar diffraction due to the porous architecture of the nanofibers, the oil medium of FIG. 15B minimizes diffraction with near homogenous medium due to the matched refractive index of the SU-8 ($n_{SU-8}$=1.67) and the oil medium ($n_{oil}$=1.47). FIGS. 15C and 15D show SEM images of examples of patterned nanofiber pillars that were fabricated in air and oil mediums, respectively. The oil medium increases the height from 25.91±4.13 μm to 55.50±3.32 μm with a dose of 400 mJ/cm$^2$, while decreasing the diameter from 100.8±24.08 μm to 73.28±5.85 μm for a 60 μm pattern diameter giving an aspect ratio (height to width) of 0.76.

Figure 16A:
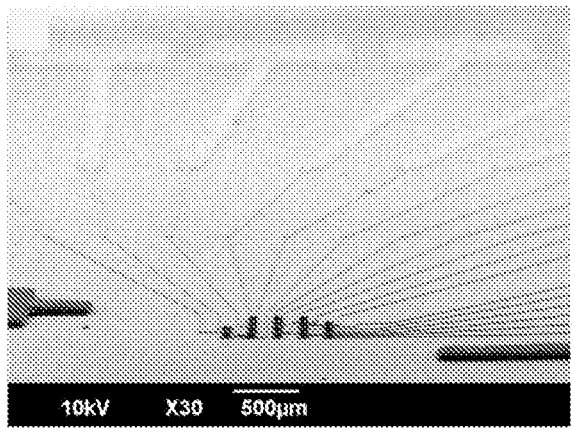
Figure 16B:
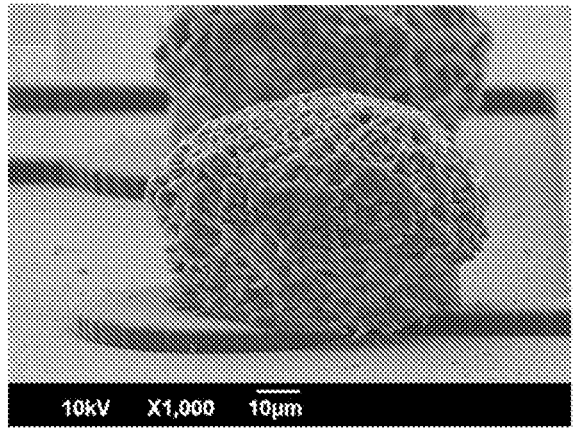

The fabricated CNF based microelectrode arrays are demonstrated in FIGS. 16A-16F. In FIG. 16A, readout electrode pads and nanofiber pillars fabricated of SU-8 are clearly delineated from the quartz wafer background in the image. Two pillar diameters were used in the fabrication of the nanofiber electrodes, 60 μm and 30 μm, on 60 μm diameter trace electrode pads interfacing the nanofiber patterns with the readout electrodes. FIG. 16B shows an SEM image of the patterned (but slightly misaligned) 60 μm nanofiber pillars on the SU-8 thin film pads. Using an exposure dosage of 300 mJ/cm$^2$, the nanofiber pillars were produced with an average height and diameter of 43.5±3.8 μm and 68.5±9.5 μm, respectively.

Figure 16C:
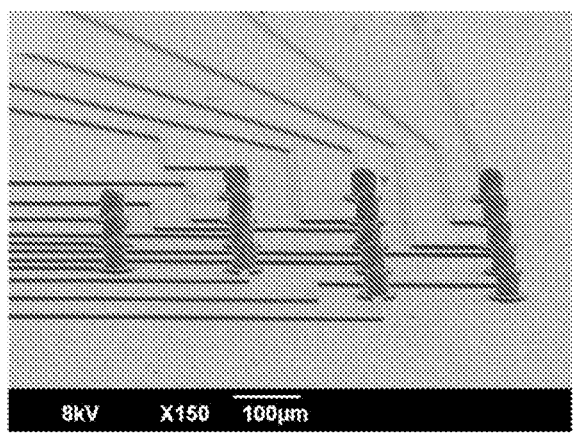
Figure 16D:
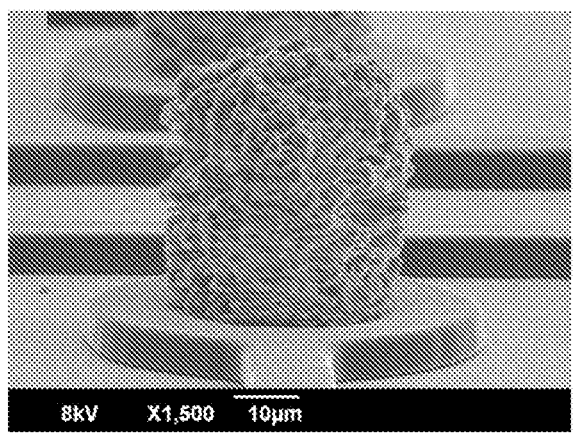

FIG. 16C shows well aligned patterns of 30 μm diameter nanofiber pillars on SU-8 trace electrodes and FIG. 16D shows a side view of one of the 30 μm nanofiber pillars with near vertical cross-sections. Using a dosage of 500 mJ/cm$^2$ produced a nanofiber pillar height and diameter of 37.3±2.5 μm and 35.1±2.3 μm, respectively. As previously discussed, the narrower mask pattern (d=30 μm) requires a higher exposure dosage when compared to the wider mask pattern (d=60 μm) for similar height of nanofibers. This may be attributed to the increased reflectivity of the smaller mask patterns, which reduces dosage to the nanofibers.

Figure 16E:
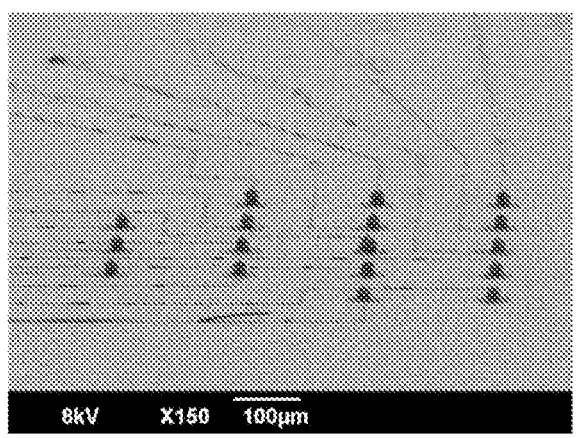
Figure 16F:
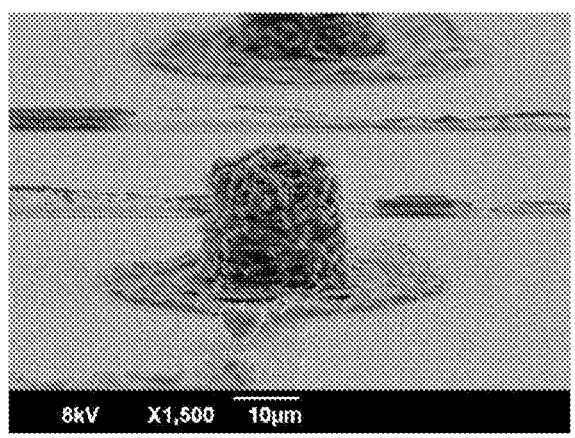

FIG. 16E shows an SEM image of the carbon nanofiber (CNF) pillars and carbon thin film (CTF) trace electrodes from FIG. 16C after the carbonization process was carried out on the 30 μm nanofiber pillars. The shrinkage in size of the structures is observable in both the CNF pillars and CTF trace electrodes with the overall patterns still preserved. In the image of FIG. 16F, the porous architecture of the nanofiber structure in FIG. 16D remains intact in the CNF pillar, while the carbon thin film formed a flaky but continuous structure in the CTF trace electrodes. The decreased structural integrity of carbon thin film may be attributed to the combined effect of under exposure of the SU-8 thin film and edge delamination of the SU-8 thin film during the chrome etching phase.

FIGS. 17A through 17I demonstrate the intermediate steps of the fabrication process of patterned MEAs. FIGS. 17A-17C are SEM images of patterned nanofiber pillars, formed on a quartz substrate, that were exposed with dosages of 300 mJ/cm$^2$, 400 mJ/cm$^2$ and 500 mJ/cm$^2$, respectively. Not only does the nanofiber pillar height increase with the increasing exposure dosage, but the profile of the nanofiber pillar also changes from a tapered to a bulbous structure.

For FIGS. 17D-17F, an SU-8 TF (STF) was introduced between the quartz substrate and the nanofiber pillars and exposed with dosages of 300 mJ/cm$^2$, 400 mJ/cm$^2$ and 500 mJ/cm$^2$, respectively. As can be observed in FIGS. 17D-17F, the heights of the patterned nanofiber pillars were less than the patterned nanofiber pillars in FIGS. 17A-17C without the STF. The decreased height of patterned nanofiber when the STF was present may be attributed to about 5% to about 10% transmission loss of UV light in cross-linked SU-8 for 365 nm. The SEM images of FIGS. 17G-17I show the SNF-STF structures of FIGS. 17D-17F after carbonization to produce CNF-CTF architectures. The height and the diameter of the CNF pillars decreased. For carbonized thin film on the substrate, the height of the thin film decreased but not the width.

Quantitative analysis of height and diameter of nanofiber pillars in the intermediate stages at incremental exposure dosages is shown in FIGS. 18A and 18B, respectively. For the SNF pillars formed directly on the substrate, the nanofiber height (curve 1803 of FIG. 18A) increased from 11.6±1.1 μm to 43.03±1.2 μm for exposure dosages from 100 mJ/cm$^2$ to 500 mJ/cm$^2$, and the diameter (curve 1806 of FIG. 18B) increased from 29.3±1.9 μm to 38.6±3.6 μm.

Where STF is located between the nanofiber and the mask, the height of the nanofibers (curve 1809 of FIG. 18A) decreased by an average of 8.4±4.1 μm and the diameter of the nanofibers (curve 1812 of FIG. 18B) decreased by an average of 3.4±0.5 μm when compared to the SNF pillars without the STF for the same exposure dosage. With the carbonization process, the CNF pillar height (curve 1815 of FIG. 18A) and diameter (curve 1818 of FIG. 18B) further shrinks by 65.0% and 46.7%, respectively.

FIGS. 19A-19F shows images of cultures of E18 rat neurons on fabricated nanofiber MEAs. The images of FIGS. 19A-19C include 7-day in vitro E18 rat cortical neuronal culture on nanofiber MEAs with heights of 10 μm (FIG. 19A), 12.5 μm (FIG. 19B), and 15 μm (FIG. 19C). FIGS. 19D-19F show fluorescence imaging for each of the nanofiber heights at 10 μm (FIG. D), 12.5 μm (FIG. 19E), and 15 μm (FIG. 19F). Cells were observed to adhere well to the nanofiber electrodes arrays with most of the cells preferring the periphery of the patterned electrodes. Multiple cell density clusters were observed on single electrode patterns with the highest density observed in the case of 12.5 μm thick nanofiber pillars of FIGS. 19B and 19E. Neural outgrowth was observed to prefer sharp edges of the thin film electrodes as long strands of neurons were observed traversing the length of the line patterns. In FIG. 19F, neuronal outgrowth was observed in long lines corresponding to the underlying trace electrodes formed of carbon thin film.

Figure 20:
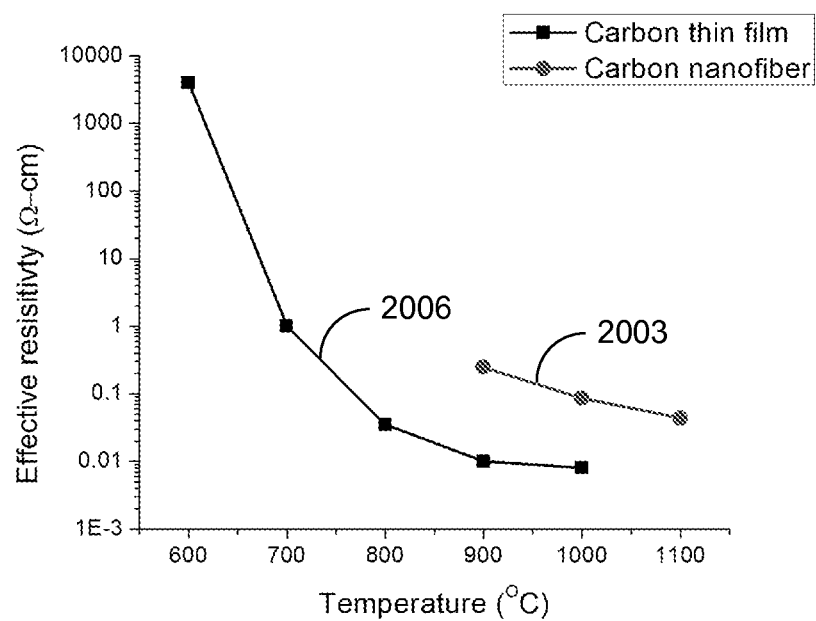
FIG. 20 is a plot of measured effective resistivity of CNF membranes at different final carbonization temperatures in comparison with carbon thin films, in accordance with various embodiments of the present disclosure.

FIG. 20 shows the measured effective resistivity of CNF membranes at different final carbonization temperatures in comparison with that of carbon thin film. For the CNF structures, the resistivity (curve 2003) decreased as the final process temperatures increased, with the highest resistivity of CNFs formed at 900° C. measured to be 0.247 Ω-cm and the lowest resistivity of CNFs formed at 1100° C. measured to be 0.044 Ω-cm. The decrease in the CNF resistivity is similar to that of CTF (curve 2006). But the CNFs were observed to have a higher resistivity than that of CTFs, which may be attributed to the increased porosity of the CNFs.

Nanofiber microelectrode arrays have been fabricated using immersion lithography of electrospun nanofibers. High aspect ratio pillars were fabricated on thin film SU-8 and carbonized to give high aspect ratio carbon nanofiber pillars. Experimental data with different exposure dosages without and with thin film SU-8 were demonstrated. Cell culture on the fabricated MEAs demonstrated increased cell viability of neurons on carbon nanofibers and increased cell density on the periphery of the patterned nanofibers. Preferential growth of neurons was observed along the length of patterned thin film.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1 wt % to about 5 wt %, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:
1. A method, comprising:
electrospinning photosensitive nanofibers on a patterned substrate, the patterned substrate comprising a substrate transparent to ultraviolet (UV) light, the substrate having a first surface and a second surface, the patterned substrate comprising a patterned photomask disposed on the first surface of the substrate, the photosensitive nanofibers spun on the patterned substrate in a layer over the patterned photomask disposed on the first surface of the substrate, the layer of photosensitive nanofibers in contact with at least a portion of the first surface of the substrate, the layer of the photosensitive nanofibers having voids between the photosensitive nanofibers;

immersing the layer of the photosensitive nanofibers in a refractive index matching medium prior to any baking of the photosensitive nanofibers, where the refractive index matching medium fills the voids between the immersed photosensitive nanofibers spun on the patterned substrate; and exposing the immersed photosensitive nanofibers to UV light directed through the substrate from the second surface to the first surface, the UV light passing through the substrate and into the layer of photosensitive nanofibers via the patterned photomask on the first surface of the substrate.

2. The method of claim 1, further comprising forming a thin film trace pattern on the patterned substrate before electrospinning the photosensitive nanofibers, the thin film trace pattern formed of a photosensitive thin film disposed on the patterned photomask and portions of the first surface of the substrate, wherein the photosensitive nanofibers are electrospun on the thin film trace pattern and the patterned substrate.

3. The method of claim 2, wherein forming the thin film trace pattern comprises:

spin coating the photosensitive thin film on the patterned photomask and the portions of the first surface of the substrate; and patterning the photosensitive thin film to form the thin film trace pattern of the photosensitive thin film, the photosensitive thin film patterned by exposure through a trace mask disposed over the photosensitive thin film opposite the patterned substrate.

4. The method of claim 3, wherein the thin film trace pattern comprises a plurality of electrode pads formed of the photosensitive thin film.

5. The method of claim 2, wherein a portion of the immersed photosensitive nanofibers are exposed to the UV light through the thin film trace pattern.

6. The method of claim 3, wherein the photosensitive thin film comprises photosensitive epoxy.

7. The method of claim 6, wherein the photosensitive epoxy is SU-8 photoresist.

8. The method of claim 1, wherein the photosensitive nanofibers are electrospun from photosensitive epoxy.

9. The method of claim 8, wherein the photosensitive epoxy is SU-8 photoresist.

10. The method of claim 1, further comprising forming the patterned photomask on the first surface of the substrate.

11. The method of claim 10, wherein the patterned photomask comprises chrome sputtered on the first surface of the substrate.

12. The method of claim 1, wherein the substrate is a quartz substrate.

13. The method of claim 1, further comprising:

forming a reservoir on the patterned substrate around the layer of the photosensitive nanofibers; and filling the reservoir with the refractive index matching medium to immerse the layer of the photosensitive nanofibers in the refractive index matching medium.

14. The method of claim 1, further comprising developing the photosensitive nanofibers after exposure to the UV light to remove unexposed portions of the photosensitive nanofibers.

15. The method of claim 14, further comprising baking the photosensitive nanofibers to form carbon nanofiber pillars having an aspect ratio greater than or equal to 0.4.

16. The method of claim 15, wherein a thin film trace pattern is formed on the patterned substrate from a photosensitive thin film disposed on the patterned photomask and portions of the first surface of the substrate before electrospinning the photosensitive nanofibers, wherein the photosensitive nanofibers are electrospun on the thin film trace pattern and the patterned substrate and the baking forms carbon thin film electrode pads from the photosensitive thin film disposed between exposed portions of the photosensitive nanofibers and the patterned substrate.

17. The method of claim 15, further comprising etching the patterned photomask formed from a chrome layer disposed on the first surface of the substrate to remove at least a portion of the chrome layer between patterned carbon thin film electrode traces formed on the chrome layer, wherein the carbon nanofiber pillars are formed on at least a portion of the patterned carbon thin film electrode traces.

18. A microelectrode array, comprising:

a patterned substrate comprising a patterned photomask disposed on a surface of a substrate;

a carbon thin film (CTF) trace pattern disposed on at least a portion of the patterned photomask, the CTF trace pattern including a plurality of CTF electrode pads formed from a photosensitive thin film disposed over the patterned photomask opposite the substrate; and a plurality of carbon nanofiber (CNF) pillars disposed on the plurality of CTF electrode pads on the substrate.

19. The microelectrode array of claim 18, wherein the plurality of CNF pillars have an aspect ratio of greater than or equal to 0.4.

20. The microelectrode array of claim 18, wherein the plurality of CTF electrode pads have a diameter greater than a diameter of the plurality of CNF pillars.

* * * * *